(12) United States Patent
Baranowska-Kortylewicz et al.

(10) Patent No.: US 11,607,464 B2
(45) Date of Patent: Mar. 21, 2023

(54) COMPOSITIONS AND METHODS FOR THE TREATMENT AND IMAGING OF CANCER

(71) Applicant: BOARD OF REGENTS OF THE UNIVERSITY OF NEBRASKA, Lincoln, NE (US)

(72) Inventors: Janina Baranowska-Kortylewicz, Omaha, NE (US); Zbigniew Kortylewicz, Omaha, NE (US)

(73) Assignee: BOARD OF REGENTS OF THE UNIVERSITY OF NEBRASKA, Lincoln, NE (US)

( * ) Notice: Subject to any disclaimer, the term of this patent is extended or adjusted under 35 U.S.C. 154(b) by 200 days.

(21) Appl. No.: 16/967,527

(22) PCT Filed: Apr. 4, 2019

(86) PCT No.: PCT/US2019/025813
§ 371 (c)(1),
(2) Date: Aug. 5, 2020

(87) PCT Pub. No.: WO2019/195566
PCT Pub. Date: Oct. 10, 2019

(65) Prior Publication Data
US 2021/0228747 A1    Jul. 29, 2021

Related U.S. Application Data

(60) Provisional application No. 62/652,543, filed on Apr. 4, 2018.

(51) Int. Cl.
| | | |
|---|---|---|
| A61K 51/04 | (2006.01) | |
| A61P 35/00 | (2006.01) | |
| A61K 31/4184 | (2006.01) | |
| A61B 6/03 | (2006.01) | |
| A61N 5/10 | (2006.01) | |
| C07D 235/32 | (2006.01) | |

(52) U.S. Cl.
CPC .......... *A61K 51/0453* (2013.01); *A61B 6/037* (2013.01); *A61K 31/4184* (2013.01); *A61N 5/1007* (2013.01); *A61P 35/00* (2018.01); *C07D 235/32* (2013.01); *C07B 2200/05* (2013.01)

(58) Field of Classification Search
CPC ............................... A61K 51/04; A61P 35/00
See application file for complete search history.

(56) References Cited

U.S. PATENT DOCUMENTS

| 8,211,656 B2 | 7/2012 | Hyde et al. | |
|---|---|---|---|
| 2011/0176998 A1* | 7/2011 | Pomper | A61K 51/0491 424/1.73 |
| 2016/0287728 A1 | 10/2016 | Norenberg | |

OTHER PUBLICATIONS

ZbigniewP.Kortylewicz et al.,RadioiodinatedAgentsforImagingMutidrugResistantTumors,MedicinalChemistry,5,171-181.(Year: 2009).*
Kortylewicz, et al., "Radiosynthesis of microtubule-targeted theranostic methyl N-[5-(3'-radiohalobenzoyl)-1H-benzimidazol-2-yl] carbamates" J. Label Compd. Radiopharm. (2018) 61:749-756.
Zhang, et al., "Design and synthesis of a novel candidate compound NTI-007 targeting sodium taurocholate cotransporting polypeptide [NTCP]-APOA1-HBx-Beclin1-mediated autophagic pathway in HBV therapy" Bioorg. Med. Chem. (2015) 23:976-984.
Korde, et al., "99mTc-labeling of colchicine using [99mTc(CO)3(H2O)3]+ and [99mTcN]2+ core for the preparation of potential tumor-targeting agents" Bioorganic & Medicinal Chemistry (2006) 14:793-799.
Zareneyrizi, et al., "Synthesis of [99mTc]ethyjenedicysteine-colchicine for evaluation of antiangiogenic effect" Anti-Cancer Drugs (1999) 10(7):685-692.
Kortylewicz, et al., "Biological Evaluation of a Potential Anticancer Agent Methyl N-[5-(3¢-Iodobenzoyl)-1HBenzimidazol-2-yl]Carbamate" Cancer Biotherapy and Radiopharmaceuticals (2020) 35(1):16-25.

* cited by examiner

*Primary Examiner* — Michael G. Hartley
*Assistant Examiner* — Jagadishwar R Samala
(74) *Attorney, Agent, or Firm* — Robert C. Netter, Jr.; Dann, Dorfman, Herrell & Skillman

(57) ABSTRACT

Compositions and methods for treating, detecting, and diagnosing cancer are disclosed.

17 Claims, 11 Drawing Sheets

COMPOSITIONS AND METHODS FOR THE TREATMENT AND IMAGING OF CANCER

This application is a § 371 application of PCT/US2019/025813, filed Apr. 4, 2019, which claims priority under 35 U.S.C. § 119(e) to U.S. Provisional Patent Application No. 62/652,543, filed on Apr. 4, 2018. The foregoing applications are incorporated by reference herein.

This invention was made with government support under Grant No. R21 CA187548 awarded by the National Institutes of Health. The government has certain rights in the invention.

FIELD OF THE INVENTION

The present invention relates to the field of chemotherapeutics and cancer imaging agents. Specifically, the instant invention provides novel chemotherapeutic and imaging agents and methods of use thereof.

BACKGROUND OF THE INVENTION

Several publications and patent documents are cited throughout the specification in order to describe the state of the art to which this invention pertains. Full citations of these references can be found throughout the specification. Each of these citations is incorporated herein by reference as though set forth in full.

Drugs that target the cytoskeleton and spindle apparatus of tumor cells belong to one of the most important classes of chemotherapeutics (Von Hoff, D. D., Semin. Oncol. (1997) 24:S13-3-S-10; Yadav, et al., Anticancer Agents Med. Chem. (2016) 16(11):1403-1425; Hanusova, et al., Curr. Cancer Drug Targets (2015) 15(1):35-52; Dumontet, et al., Nat. Rev. Drug Discov. (2010) 9(10):790-803; Geney, et al., Med. Chem. (2005) 1(2):125-139). Functional microtubules are essential for proliferation, invasion and migration of cancer cells. Microtubule-binding drugs such as taxanes, vinca alkaloids and epothilones are widely used as the standard first-line option treatment in many cancers (Yadav, et al., Anticancer Agents Med. Chem. (2016) 16(11):1403-1425; Sasaki, et al., Mol. Cancer Ther. (2002) 1(13):1201-1209; Stanton, et al., Med. Res. Rev. (2011) 31(3):443-481), but their utility is frequently limited by significant toxicities and primary or acquired resistance. Novel microtubule targeting drugs, particularly ones with decreased toxicity and decreased acquired resistance, are needed for the treatment of cancer.

SUMMARY OF THE INVENTION

In accordance with the instant invention, benzimidazol-2-yl-carbamates are provided. In a particular embodiment, the compound is a methyl N-[5-benzoyl-1H-benzimidazol-2-yl]carbamate, particularly a methyl N-[5-(3'-halobenzoyl)-1H-benzimidazol-2-yl]carbamate, methyl N-[5-(3'-iodobenzoyl)-1H-benzimidazol-2-yl]carbamate, methyl N-[5-(3'-radioiodobenzoyl)-1H-benzimidazol-2-yl]carbamate, or methyl N-[5-(3'-radiohalobenzoyl)-1H-benzimidazol-2-yl]carbamate. In a particular embodiment, the compound has the structure presented in formula (I), wherein R is selected from the group consisting of optionally substituted alkyl or aliphatic, optionally substituted aryl, halogen, and an isotope. In a particular embodiment, R is a halogen or an isotope. The isotope may be a stable isotope or a radioisotope. In a particular embodiment, R is an isotope of a halogen or a radiohalide such as $^{18}F$, $^{74}Br$, $^{75}Br$, $^{76}Br$, $^{77}Br$, $^{81}Br$, $^{123}I$, $^{124}I$, $^{125}I$, $^{127}I$, $^{131}I$, or $^{211}At$.

In accordance with another aspect of the instant invention, compositions comprising a compound of the instant invention and a pharmaceutically acceptable carrier are also provided. The composition may further comprise an anticancer therapeutic agent.

In accordance with another aspect of the instant invention, methods of treating, inhibiting, and/or preventing a cancer in a subject are provided. In a particular embodiment, the method comprises administering a compound of the instant invention or composition comprising the same to the subject. In a particular embodiment, the compound is non-radioactive and, optionally, administered with radiation therapy to the subject. In a particular embodiment, the compound comprises a radioactive isotope.

In accordance with another aspect of the instant invention, methods for imaging and/or detecting a tumor or cancerous tissue in a subject a subject. In a particular embodiment, the method comprises administering a compound of the instant invention, particularly one comprising a radioactive isotope, to the subject and determining the location of the radioactivity within the subject. In a particular embodiment, the radioactive isotope is a gamma emitting isotope and the method comprises performing a single photon emission computed tomography (SPECT) or scintigraphy to detect the gamma radiation. In a particular embodiment, the radioactive isotope is a positron emitting isotope and the method comprises performing a positron emitting tomography (PET) to detect the positron radiation. The detection step can be performed at more than one timepoint (optionally after an additional administration of the compound) to monitor the progression of a cancer or response to a therapy in a subject.

BRIEF DESCRIPTION OF THE DRAWINGS

FIG. 2A: The reaction mixture analyzed after 21 minutes. FIG. 2B: The reaction mixture analyzed after 68 minutes. FIG. 2C: Purified $^{125}I$-4 (92 kBq) obtained in the direct radioiodination of 1 and co-injected with nonradioactive iodo-derivative 2 (4.6 μg) in 25 μL MeCN.

FIG. 3A: Purification of the crude destannylation mixture of 3 reacted with 70.3 MBq Na$^{125}I$. FIG. 3B: HPLC analysis of the isolated $^{125}I$-4. FIG. 3C: The exchange of solvents for $^{125}I$-4 (166 kBq) using the HPLC system.

FIG. 4A: $^{125}I$-4 in human serum after a 5 hour incubation at 20° C. FIG. 4B: $^{125}I$-4 incubated at 37° C. in human serum for 17 hours. FIG. 4C: $^{125}I$-4 incubated in Eagle's Minimum Essential Medium (EMEM) cell culture medium at 37° C. in 5% $CO_2$/air atmosphere for 19 hours.

DETAILED DESCRIPTION OF THE INVENTION

Figure 1:
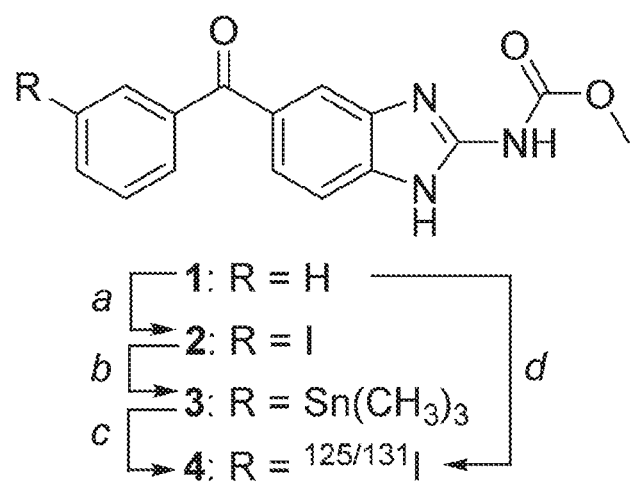
FIG. 1 shows radioiodination pathways used to produce methyl N-[5-(3'-radiohalobenzoyl)-1H-benzimidazol-2-yl]carbamates 4.

Microtubules are a target for a broad spectrum of drugs used as chemotherapeutics to treat hematological malignancies and solid tumors. Most of these drugs have significant dose-limiting toxicities including peripheral neuropathies that can be debilitating and permanent. In an ongoing effort to develop safer and more effective drugs, benzimidazole-based compounds are being developed as replacement for vincristine and similar agents. Several benzimidazoles have microtubule-disrupting properties as well as anti-proliferative effects in cancer cell lines and in animal models (Yadav, et al., Anticancer Agents Med. Chem. (2016) 16(11):1403-1425; Pantziarka, et al., Ecancermedicalscience (2014) 8:443; Spagnuolo, et al., Blood (2010) 115(23):4824-4833). Herein, novel benzimidazol-2-yl-carbamates (e.g., methyl N-[5-(3'-radiohalobenzoyl)-1H-benzimidazol-2-yl]carbamates and methyl N-[5-(3'-halobenzoyl)-1H-benzimidazol-2-yl]carbamates) have been prepared. These compounds can be used as imaging agents and molecular radiotherapeutics. For example, the new drugs can be radiolabeled without reshaping their chemical structure with, for example, either positron- and γ-emitting radiohalides for imaging, or α- and β-particle-emitting radiohalides for molecular radiotherapy.

In the age of personalized treatments, it is important to quantify the uptake of a drug by the tumor as well as normal tissues to assess the efficacy and potential off-target toxicity. The ability to measure radiation doses delivered by the radiolabeled drug to tumors can help to predict patient's response to the treatment. Only a few attempts have been made to develop microtubule-targeted imaging agents (Korde, et al., Bioorg. Med. Chem. (2006) 14(3):793-799; Zareneyrizi, et al., Anticancer Drugs (1999) 10(7):685-692). Recently, $^{11}$C-docetaxel was synthesized and evaluated in cancer patients to directly measure docetaxel concentrations in tumor and facilitate rational treatment choices (van der Veldt, et al., Eur. J. Nucl. Med. Mol. Imaging (2010) 37(10):1950-1958; van der Veldt, et al., Clin. Cancer Res. (2011) 17(14):4814-4824). Here, the novel microtubule-targeted radiopharmaceuticals can be used as imaging as well as radiotherapeutic agents and can enable distribution assessments of the nonradioactive analogues.

The compounds of the instant invention (e.g., methyl N-[5-(3'-radiohalobenzoyl)-1H-benzimidazol-2-yl]carbamates) can be synthesized by different methods. For example, $^{125}$I- and $^{131}$I-radiolabeled derivatives were prepared either by direct radioiodination of methyl N-(6-benzoyl-1H-benzimidazol-2-yl)carbamate 1 or radioiododestannylation of the corresponding stannane precursor 3. The direct radioiodination was conducted in a solution of 1 in triflic acid and produced after ~1 hour at elevated temperatures and HPLC purification on average 62% of the no-carrier added products $^{125}$I-4 and $^{131}$I-4. Radioiododestannylation of 3'-trimethylstannane 3 proceeded with ease at room temperature in the presence of $H_2O_2$ as the oxidant and produced no-carrier-added $^{125}$I-4 and $^{131}$I-4 in high isolated yields, on average 85%. The radiohalodestannylation protocol is universal and can be applied to other radiohalides including, without limitation, $^{124}$I to produce $^{124}$I-4 a positron emission tomography agent, and $^{211}$At to produce $^{211}$At-4, an α-particle emitting radiotherapeutic.

In accordance with the instant invention, novel benzimidazol-2-yl-carbamates are provided. In a particular embodiment, the compound is a methyl N-[5-benzoyl-1H-benzimidazol-2-yl]carbamate, particularly a methyl N-[5-(3'-halobenzoyl)-1H-benzimidazol-2-yl]carbamate, methyl N-[5-(3'-iodobenzoyl)-1H-benzimidazol-2-yl]carbamate, methyl N-[5-(3'-radioiodobenzoyl)-1H-benzimidazol-2-yl]carbamate, or methyl N-[5-(3'-radiohalobenzoyl)-1H-benzimidazol-2-yl]carbamate. In a particular embodiment, the compound of the present invention is of formula (I) or a pharmaceutically acceptable salt thereof:

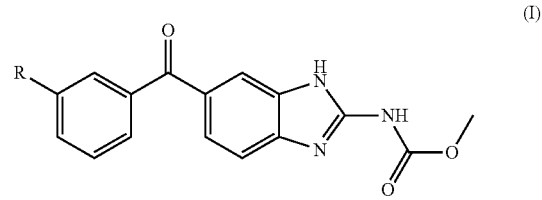

(I)

wherein R is selected from the group consisting of H, optionally substituted alkyl or aliphatic, optionally substituted aryl, halogen, and an isotope. In a particular embodiment, R is not H. The isotope may be a stable isotope (e.g., non-radioactive isotope or stable nuclide) or a radioisotope (e.g., radionuclide). In a particular embodiment, R is a radioisotope. In a particular embodiment, the isotope is an isotope (e.g., a radioisotope) of a halogen (e.g., F, Cl, Br, I, or At), particularly an isotope (e.g., a radioisotope) of F (e.g., $^{18}$F), Br (e.g., $^{74}$Br, $^{75}$Br, $^{76}$Br, $^{77}$Br, or $^{81}$Br), I (e.g., $^{123}$I, $^{124}$I, $^{125}$I, $^{127}$I, or $^{131}$I), or At (e.g., $^{211}$At).

Radioisotopes include, without limitation, positron-emitting isotopes and alpha-, beta-, gamma-, Auger- and low energy electron-emitters. A radioisotope may emit more than one type of radiation. In a particular embodiment, R is a radiohalide (e.g., a radioisotope of a halogen), particularly a radioisotope of Br, I, or At. In a particular embodiment, R is a radioisotope of Br (e.g., $^{74}$Br, $^{75}$Br, $^{76}$Br, or $^{77}$Br). In a particular embodiment, R is a radioisotope of I (e.g. $^{123}$I, $^{124}$I, $^{125}$I, or $^{131}$I). In a particular embodiment, R is a radioisotope of At (e.g., $^{211}$At). Examples of radioisotopes include, without limitation: $^{11}$C, $^{13}$N, $^{18}$F, $^{32}$P, $^{64}$Cu, $^{66}$Ga, $^{67}$Ga, $^{68}$Ga, $^{67}$Cu, $^{74}$Br, $^{75}$Br, $^{76}$Br, $^{77}$Br, $^{80m}$Br, $^{82}$Rb, $^{86}$Y, $^{89}$Sr, $^{89}$Zr, $^{90}$Y, $^{95}$Ru, $^{97}$Ru, $^{99m}$Tc, $^{103}$Ru, $^{105}$Ru, $^{111}$In, $^{113m}$In, $^{113}$Sn, $^{121m}$Te, $^{122m}$Te, $^{125m}$Te, $^{123}$I, $^{124}$I, $^{125}$I, $^{126}$I, $^{131}$I, $^{133}$I, $^{165}$Tm, $^{167}$Tm, $^{168}$Tm, $^{177}$Lu, $^{186}$Re, $^{188}$Re, $^{195m}$Hg, $^{211}$At, $^{212}$Pb, $^{212}$Bi, $^{213}$Bi, $^{223}$Ra, and $^{225}$Ac.

In accordance with the instant invention, compositions and methods for inhibiting (e.g., reducing or slowing), treating, and/or preventing cancer in a subject are provided. In a particular embodiment, the methods comprise administering to a subject in need thereof at least one compound of the instant invention. In a particular embodiment, the compound is a benzimidazol-2-yl-carbamate, particularly a methyl N-[5-benzoyl-1H-benzimidazol-2-yl]carbamate, methyl N-[5-(3'-halobenzoyl)-1H-benzimidazol-2-yl]carbamate, methyl N-[5-(3'-iodobenzoyl)-1H-benzimidazol-2-yl]carbamate, methyl N-[5-(3'-radioiodobenzoyl)-1H-benzimidazol-2-yl]carbamate, or methyl N-[5-(3'-radiohalobenzoyl)-1H-benzimidazol-2-yl]carbamate, or a compound of formula (I). In one embodiment, the compound used to treat cancer is a non-radioactive compound (i.e., R does not contain a radioactive isotope). As described herein, the non-radioactive compound of the instant invention is cytotoxic on its own and may be used as a radiosensitizer. In another embodiment, the compound used to treat cancer contains a radioactive isotope (e.g., R comprises a radioactive isotope). In a particular embodiment, the radioactive isotope is an alpha emitter (e.g., $^{211}$At, $^{212}$Pb, $^{212}$Bi, $^{213}$Bi, $^{223}$Ra, $^{225}$Ac, etc.). In a particular embodiment, the radioactive isotope is a beta emitter (e.g., $^{64}$Cu, $^{86}$Y, $^{89}$Sr, $^{89}$Zr, $^{90}$Y, $^{124}$I, $^{131}$I, $^{177}$Lu, $^{188}$Re, etc.). In a particular embodiment, the radioactive isotope is an Auger emitter (e.g., $^{77}$Br, $^{111}$In, $^{123}$I, $^{125}$I, etc.). In a particular embodiment, the radioisotope is selected from the group consisting of $^{74}$Br, $^{75}$Br, $^{76}$Br, $^{77}$Br, $^{123}$I, $^{124}$I, $^{125}$I, $^{131}$I, and $^{211}$At. The compounds of the present invention can be used to directly kill cancer cells. The compounds may also be used to increase the radiosensitivity of cancer cells making them more susceptible to radiation.

The methods of the instant invention can be used to inhibit, prevent, and/or treat any cancer in a subject in need thereof, particularly a human. In a particular embodiment, the cancer is a solid tumor. In a particular embodiment, the cancer is a hematological cancer. The cancer may be chemo-resistant and/or radio-resistant. Examples of cancer that can be treated by the methods of the instant invention include, without limitation: leukemia (e.g., acute lymphoblastic leukemia, acute myeloid leukemia, chronic lymphocytic leukemia, chronic myelogenous leukemia), lymphoma (e.g., Hodgkin lymphoma, Non-Hodgkin lymphoma), multiple myeloma, breast cancer, prostate cancer, pancreatic cancer, colon cancer, thyroid cancer, bladder cancer, liver cancer, neuroendocrine tumor, neuroblastoma, brain cancers (e.g., gliomas, glioblastoma (e.g., glioblastoma multiforme), meningiomas, pituitary adenomas, medulloblastoma etc.), lung cancer, esophageal cancer, ovarian cancer, stomach cancer, skin cancer (e.g., melanoma), cervical cancer, testicular cancer, kidney cancer, carcinoid tumors, and bone cancer. In a particular embodiment, the cancer is elected from the group consisting of ovarian cancer, breast cancer, prostate cancer, colon cancer, liver cancer, brain cancer, kidney cancer, lung cancer, leukemia, lymphoma, multiple myeloma, thyroid cancer, bone cancer, esophageal cancer, neuroendocrine tumor, neuroblastoma, and pancreatic cancer. In a particular embodiment, the cancer is neuroblastoma, medulloblastoma, or glioblastoma, particularly neuroblastoma.

The methods may further comprise the administration of at least one other cancer therapy to the subject. Examples of additional therapies include, without limitation: surgery (e.g., tumor excision), chemotherapies (chemotherapeutic agents), immunotherapies, cell therapies, targeted therapy (e.g., small molecule inhibitors, antibodies), radiosentizer, and radiation therapy (e.g., external beam radiation, ionizing radiation, radiopharmaceuticals). The compound of the instant invention may be administered to a subject consecutively (e.g., before and/or after) and/or simultaneously with another therapy for treating, inhibiting, and/or preventing the cancer in the subject. In a particular embodiment, the compound of the instant invention is administered with at least one chemotherapeutic agent.

In a particular embodiment, the compound of the instant invention is administered with at least radiation therapy. As demonstrated hereinbelow, the compounds of the instant invention are radiosensitizers. In a particular embodiment, the compound is a non-radioactive compound (i.e., R does not contain a radioactive isotope (e.g., R is a halide)). The treatment of certain cancers such as brain cancers (e.g., medulloblastoma) can be difficult with high doses of radiation therapy due to side-effects such as neurocognitive deficiencies, hormone deficits, and growth impairment. In the pediatric patient population, neural toxicity to the developing brain greatly limits treatment options. The compounds of the instant invention, particularly nonradioactive compounds, can be used as a radiosensitizer to greatly reduce the radiation dose to the subject (e.g., to the brain), thereby significantly reducing unwanted side-effects.

Chemotherapeutic agents are compounds that exhibit anticancer activity and/or are detrimental to a cell (e.g., a toxin). Suitable chemotherapeutic agents include, but are not limited to: toxins (e.g., saporin, ricin, abrin, ethidium bromide, diptheria toxin, *Pseudomonas* exotoxin, and others listed above; thereby generating an immunotoxin when conjugated or fused to an antibody); alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nitroso ureas such as carmustine, lomustine, and streptozocin; platinum complexes such as cisplatin and carboplatin; bioreductive alkylators such as mitomycin, procarbazine, dacarbazine and altretamine); DNA strand-breakage agents (e.g., bleomycin); topoisomerase I inhibitor (e.g., topotecan); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate and trimetrexate); pyrimidine antagonists (analogs) such as fluorouracil (5-fluorouracil), gemcitabine, fluorodeoxyuridine, CB3717, azacitidine, cytarabine, and floxuridine; purine antagonists (analogs) such as mercaptopurine, 6-thioguanine, fludarabine, pentostatin; asparginase; ribonucleotide reductase inhibitors (such as hydroxyurea); tubulin interactive agents (e.g., vincristine, vinblastine, docetaxel, and paclitaxel (Taxol®)); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); immunomodulator (e.g., levamisole); and antihormonal antigens (e.g., tamoxifen, antiandrogen agents such as flutamide; and antiadrenal agents such as mitotane and aminoglutethimide).

Compositions comprising at least one compound of the instant invention and at least one pharmaceutically acceptable carrier are encompassed by the instant invention. Such compositions may be administered to a subject to detect and/or image cancer. Such compositions may also be administered, in a therapeutically effective amount, to a patient in need thereof for the treatment of cancer. When an additional therapy is utilized in combination with the compound of the instant invention, the compound of the instant invention may be contained within a first composition with at least one pharmaceutically acceptable carrier and the additional therapy (e.g., chemotherapeutic agent) may be contained within a second composition with at least one pharmaceutically acceptable carrier (the carriers of the two compositions may or may not be the same). Having the agents in separate compositions allows for ease of sequential and/or simultaneous administration. The instant invention also encompasses kits comprising at least one composition comprising at least one compound of the instant invention and at least one composition comprising at least one additional therapy (e.g., chemotherapeutic agent).

The compounds and compositions of the present invention can be administered by any suitable route, for example, by injection (e.g., for local (direct, including to or within a tumor) or systemic administration), oral, pulmonary, topical, nasal or other modes of administration. The composition may be administered by any suitable means, including intratumoral, parenteral, intramuscular, intravenous, orally, intraarterial, intraperitoneal, subcutaneous, topical, inhalatory, transdermal, intrapulmonary, intraareterial, intrarectal, intramuscular, and intranasal administration. In a particular, the compounds and compositions of the present invention are administered by direct injection (e.g., to the tumor and/or the surrounding area).

In general, the pharmaceutically acceptable carrier of the composition is selected from the group of diluents, preservatives, solubilizers, emulsifiers, adjuvants and/or carriers. The compositions can include diluents of various buffer content (e.g., Tris HCl, acetate, phosphate), pH and ionic strength; and additives such as detergents and solubilizing agents (e.g., polysorbate 80), anti oxidants (e.g., ascorbic acid, sodium metabisulfite), preservatives (e.g., Thimersol, benzyl alcohol) and bulking substances (e.g., lactose, mannitol). The compositions can also be incorporated into particulate preparations of polymeric compounds such as polyesters, polyamino acids, hydrogels, polylactide/glycolide copolymers, ethylenevinylacetate copolymers, polylactic acid, polyglycolic acid, etc., or into liposomes. Such compositions may influence the physical state, stability, rate of in vivo release, and rate of in vivo clearance of components of a pharmaceutical composition of the present invention. See, e.g., Remington: The Science and Practice of Pharmacy, 21st edition, Philadelphia, Pa. Lippincott Williams & Wilkins. 2005. The pharmaceutical composition of the present invention can be prepared, for example, in liquid form, or can be in dried powder form (e.g., lyophilized for later reconstitution).

As used herein, "pharmaceutically acceptable carrier" includes any and all solvents, dispersion media and the like which may be appropriate for the desired route of administration of the pharmaceutical preparation, as exemplified in the preceding paragraph. The use of such media for pharmaceutically active substances is known in the art. For example, the compounds may be formulated with an acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of the compounds in the chosen medium may be varied and the medium may be chosen based on the desired route of administration of the pharmaceutical preparation. Except insofar as any conventional media or agent is incompatible with the compounds to be administered, its use in the pharmaceutical preparation is contemplated.

Selection of a suitable pharmaceutical preparation depends upon the method of administration chosen. For example, the molecules of the invention may be administered by direct injection into any cancerous tissue or into the area surrounding the cancer. In this instance, a pharmaceutical preparation comprises the molecules dispersed in a medium that is compatible with the cancerous tissue.

As stated hereinabove, agents of the instant invention may also be administered parenterally by intravenous injection into the blood stream, or by subcutaneous, intramuscular, intratumor, intrathecal, or intraperitoneal injection. Pharmaceutical preparations for parenteral injection are known in the art. If parenteral injection is selected as a method for administering the molecules, steps should be taken to ensure that sufficient amounts of the molecules reach their target cells to exert a biological effect. The lipophilicity of the molecules, or the pharmaceutical preparation in which they are delivered, may have to be increased so that the molecules can arrive at their target locations. Methods for increasing the lipophilicity of a molecule are known in the art.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral, topical, or parenteral. In preparing the molecule in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. Dosage units may be proportionately increased or decreased based on the weight of the patient. Appropriate concentrations for alleviation of a particular pathological condition may be determined by dosage concentration curve calculations, as known in the art. The appropriate dosage unit for the administration of the molecules of the instant invention may be determined by evaluating the toxicity of the molecules in animal models. Various concentrations of pharmaceutical preparations may be administered to mice with transplanted human tumors, and the minimal and maximal dosages may be determined based on the results of significant reduction of tumor size and side effects as a result of the treatment. Appropriate dosage unit may also be determined by assessing the efficacy of the treatment in combination with other standard chemotherapies. The dosage units of the molecules may be determined individually or in combination with each chemotherapy according to greater shrinkage and/or reduced growth rate of tumors.

The pharmaceutical preparation comprising the molecules of the instant invention may be administered at appropriate intervals, for example, at least once a day or more until the pathological symptoms are reduced or alleviated, after which the dosage may be reduced to a maintenance level. The appropriate interval in a particular case would normally depend on the condition of the patient.

In accordance with another aspect of the instant invention, methods of detecting a cancer and/or monitoring/tracking the progress of a cancer and/or its treatment are provided. Methods of diagnosing and/or prognosing cancer in a subject are also provided. The methods comprise administering at least one compound of the instant invention to the subject and detecting the presence of the compound in the subject. In a particular embodiment, the compound is administered to the tumor and/or its surrounding area. The cancer may be detected in vivo (e.g., imaged). The methods can be used to detect if the administered compound is taken up by the cancerous tissue and/or the amount of the administered dose that is taken up by the cancerous tissue. This allows for the assessment of off-target toxicity and the efficacy of the therapy.

In a particular embodiment, the compound administered to the subject comprises an isotope (e.g., one that can be detected). The isotope selected for the compound should match the detection technique used to image the subject. For example, when positron emission tomography (PET) is utilized for imaging the subject, a positron-emitting isotope (e.g., $^{13}$N, $^{18}$F, $^{68}$Ga, $^{89}$Zr, $^{82}$Rb, $^{124}$I, etc.) may be conjugated to the compound of the invention (i.e., the R group). When single photon emission computed tomography (SPECT) or scintigraphy is utilized for imaging the subject, a gamma-emitting isotope (e.g., $^{99m}$Tc, $^{111}$In, $^{123}$I, $^{131}$I, etc.) may be conjugated to the compound of the invention (i.e., the R group).

As stated hereinabove, the instant methods may be used to diagnose cancer in patient and/or determine the prognosis of a patient, including stage and grade (particularly whether it is metastatic) of a tumor and its potential sensitivity to therapy (e.g., resistance to a chemotherapeutic agent). Similarly, the methods may be used to determine the efficacy of a treatment of a patient (e.g., whether the tumor and/or metastases are decreasing due an administered treatment). The methods of the invention may be performed more than once over a period of time to monitor tumor volume and/or metastases. The decrease in tumor volume as determined by imaging is indicative of remission or a successful treatment, while the lack of change in tumor volume in a patient undergoing treatment may be indicative of resistance to the therapy and/or may indicate that a different therapeutic strategy could be employed. Similarly, the gain of tumor volume in a patient over time can be indicative of recurrence.

Definitions

The following definitions are provided to facilitate an understanding of the present invention:

The singular forms "a," "an," and "the" include plural referents unless the context clearly dictates otherwise.

As used herein, the terms "host," "subject," and "patient" refer to any animal, including humans.

As used herein, "diagnose" refers to detecting and identifying a disease (e.g., cancer) in a subject. The term may also encompass assessing or evaluating the disease status (progression, regression, stabilization, response to treatment, etc.) in a patient known to have the disease.

As used herein, the term "prognosis" refers to providing information regarding the impact of the presence of cancer (e.g., as determined by the diagnostic methods of the present invention) on a subject's future health (e.g., expected morbidity or mortality, the likelihood of getting cancer and/or recurrence, drug resistance status of the cancer, and the risk of or presence of metastases). In other words, the term "prognosis" refers to providing a prediction of the probable course and outcome of a cancer or the likelihood of recovery from the cancer.

As used herein, the term "prevent" refers to the prophylactic treatment of a subject who is at risk of developing a condition (e.g., cancer or metastatic cancer) resulting in a decrease in the probability that the subject will develop the condition.

The term "treat" as used herein refers to any type of treatment that imparts a benefit to a patient afflicted with a disease, including improvement in the condition of the patient (e.g., in one or more symptoms), delay in the progression of the condition, etc. In a particular embodiment, the treatment of a cancer results in at least a reduction in the size of a tumor or cancerous tissue and/or reduction in the number and/or size of metastases.

A "therapeutically effective amount" of a compound or a pharmaceutical composition refers to an amount effective to prevent, inhibit, or treat a particular disorder or disease (e.g., cancer) and/or the symptoms thereof.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., polysorbate 80), emulsifier, buffer (e.g., Tris HCl, acetate, phosphate), water, aqueous solutions, oils, bulking substance (e.g., lactose, mannitol), excipient, auxilliary agent or vehicle with which an active agent of the present invention is administered. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients, American Pharmaceutical Association, Washington.

The term "radiosensitizer", as used herein, is defined as a molecule administered to animals in therapeutically effective amounts to increase the sensitivity of the cells to radiation. Radiosensitizers increase the sensitivity of cells to the toxic effects of radiation. Radiosensitizers include, without limitation, 2-nitroimidazole compounds, and benzotriazine dioxide compounds, halogenated pyrimidines, metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

The term "aliphatic" refers to a non-aromatic hydrocarbon-based moiety. Aliphatic compounds can be acyclic (e.g., linear or branched) or cyclic moieties (e.g., cycloalkyl) and can be saturated or unsaturated (e.g., alkyl, alkenyl, and alkynyl). Aliphatic compounds may comprise a mostly carbon main chain (e.g., 1 to about 30 carbons) and comprise heteroatoms and/or substituents (see below). The term "alkyl," as employed herein, includes saturated or unsaturated, straight or branched chain hydrocarbons containing 1 to about 30 carbons in the normal/main chain. The hydrocarbon chain of the alkyl groups may be interrupted with one or more heteroatom (e.g., oxygen, nitrogen, or sulfur). An alkyl (or aliphatic) may, optionally, be substituted (e.g. with fewer than about 8, fewer than about 6, or 1 to about 4 substituents). In a particular embodiment, the alkyl or aliphatic is a "lower alkyl" or "lower aliphatic", respectively, which contains 1 to 3 carbons in the hydrocarbon chain. Alkyl or aliphatic substituents include, without limitation, alkyl (e.g., lower alkyl), alkenyl, halo (such as F, Cl, Br, I), haloalkyl (e.g., $CCl_3$ or $CF_3$), alkoxyl, alkylthio, hydroxy, methoxy, carboxyl, oxo, epoxy, alkyloxycarbonyl, alkylcarbonyloxy, amino, carbamoyl (e.g., $NH_2C(=O)$— or NHRC(=O)—, wherein R is an alkyl), urea (—$NHCONH_2$), alkylurea, aryl, ether, ester, thioester, nitrile, nitro, amide, carbonyl, carboxylate and thiol. Aliphatic and alkyl groups having at least about 5 carbons in the main chain are generally hydrophobic, absent extensive substitutions with hydrophilic substituents.

The term "aryl," as employed herein, refers to monocyclic and bicyclic aromatic groups containing 6 to 10 carbons in the ring portion. Examples of aryl groups include, without limitation, phenyl or naphthyl, such as 1-naphthyl and 2-naphthyl, or indenyl. Aryl groups may optionally include one to three additional rings fused to a cycloalkyl ring or a heterocyclic ring. Aryl groups may be optionally substituted through available carbon atoms with, for example, 1, 2, or 3 groups selected from hydrogen, halo, alkyl, polyhaloalkyl, alkoxy, alkenyl, trifluoromethyl, trifluoromethoxy, alkynyl, aryl, heterocyclo, aralkyl, aryloxy, aryloxyalkyl, aralkoxy, arylthio, arylazo, heterocyclooxy, hydroxy, nitro, cyano, sulfonyl anion, amino, or substituted amino. The aryl group may be a heteroaryl. "Heteroaryl" refers to an optionally substituted, mono-, di-, tri-, or other multicyclic aromatic ring system that includes at least one, and preferably from 1 to about 4, sulfur, oxygen, or nitrogen heteroatom ring members. Heteroaryl groups can have, for example, from about 3 to about 50 carbon atoms (and all combinations and subcombinations of ranges and specific numbers of carbon atoms therein), with from about 4 to about 10 carbons being preferred.

The following examples are provided to illustrate various embodiments of the present invention. The examples are illustrative and is not intended to limit the invention in any way.

Example 1

Materials and Methods
Chemistry

Chemicals and reagents were purchased from commercial suppliers in the highest purity available and used without further purification. Radioiodides $Na^{131}I$ in 0.1 M NaOH (pH 12-14) and $Na^{125}I$ in $1\times10^{-5}$ M NaOH (pH 8-11) were obtained from PerkinElmer (Waltham, Mass.). Radioactivity was measured with Minaxi γ-counter (Packard, Waltham, Mass.) and a dose calibrator (Capintec Inc., Florham Park, N.J.). Compounds were separated and their purity confirmed by HPLC using Gilson (Middleton, Wis.) and ISCO (Lincoln, Nebr.) systems on 5μ, 100 Å, (250×4.6 mm), analytical or semipreparative (250×10 mm) columns, either Columbus C8, C18, Luna CN (Phenomenex, Torrance, Calif.) or ACE C18 (Advanced Chromatography Technologies, www.ace-hplc.com) eluted at rates of 0.8-2.0 mL/minute with various gradients of $CH_3CN$ or $CH_3OH$ (10%-95%) in water with (0.07%, v/v) or without trifluoroactic acid (TFA). Variable wavelength UV detectors UVIS-205 (Linear, Irvine, Calif.) or UV116 (Gilson) were used jointly with the sodium iodide crystal Bioscan Flow-Count detector connected in-line at the outlet of the UV detector. Both signals were monitored and analyzed simultaneously. The separated radiolabeled products, if kept in a solution overnight, were purified one more time shortly before conducting further experiments even though the HPLC analysis rarely indicated the radiochemical purity of less than 98%. Solutions containing final products were evaporated with a stream of nitrogen to dryness and reconstituted in a preferred solvent at the required concentration and then filtered through a sterile 0.2-μ filter (Millipore) into a sterile evacuated vial. NMR spectra were recorded in $(CD3)_2SO$ at ambient temperature on Bruker Avance III HD 600 MHz spectrometer. All NMR analyses were performed at the University of Nebraska Medical Center Eppley Institute NMR Facility (Omaha, Nebr.). Chemical shifts are given as δ (ppm) relative to TMS as internal standard with Jin hertz. High resolution electrospray ionization (ESI-HR) mass spectra were acquired on MaXis™ 4G mass spectrometer at the Washington University Resource for Biomedical and Bio-organic Mass Spectrometry (St. Louis, Mo.). Tip amounts of samples dissolved in 1 mL of 50% acetonitrile (MeCN) solution with 0.1% formic acid were analyzed under positive mode. All target nonradioactive compounds were found to be ≥95% pure by the rigorous HPLC analysis with the integration of the peak area (detected at 220 and/or 254 nm). In the consecutive radio-HPLC analyses, each purified radioiodinated product was matched with the corresponding, independently prepared, non-radioactive analogue and identified by means of the UV and radioactivity signal retention times.

Methyl N [5-(3'-iodobenzoyl)-1H-benzimidazol-2-yl]carbamate (2)

To a stirred and cooled on an ice-bath solution of methyl N-(6-benzoyl-1H-benzimidazol-2-yl)carbamate (1) (1.05 g, 3.55 mmol) in 3.5 mL of nitromethane and containing $CF_3SO_3H$ (1.50 mL, 17.07 mmol), N-iodosuccinimide (NIS, 800 mg, 3.54 mmol) was added in three small portions. The reaction temperature was gradually increased to 75° C. and kept at this temperature for an additional two hours. After cooling and evaporation of nitromethane under a high vacuum, the residue was quenched with ice-water (20 mL) and with a solution of 10% sodium bisulfite (10 mL), and then neutralized with 1 M $NaHCO_3$ to pH of ~7.5. The precipitated yellowish solid (1.12 g) was filtered off, washed with water and dried under a high vacuum. Subsequent HPLC analyses revealed a multicomponent mixture containing one major product (74%) and ~7% of the unreacted 1. After partial crystallization from MeCN, the product 2 (88.4% pure by HPLC analysis) was further purified on the HPLC system. Attempted additional recrystallizations or flash column chromatography using normal phase silica gel failed due to the quite low solubility of 2 in common solvents. A portion of the crude product (~23 mg) was purified on the HPLC (~350 µg per injection) equipped with a semipreparative Columbus C18 column (5µ, 100 Å, 10 mm×250 mm) column. Two suitable elution schemes were developed. Eluent 1: solvent A $H_2O$, solvent B MeCN; at 2.2 mL/minute flow rate a linear gradient of B from 50% to 60% in 10 minutes, then to 95% B in 12 minutes and kept at 95% B for 20 minutes; the product eluted within 15.5-17.0 minutes after the injection. Eluent 2: solvent A $H_2O$, solvent B $CH_3OH$; eluted at 2.0 mL/minute flow rate with a linear gradient of B from 40% to 82% in 18 minutes, then to 95% B in 1 minute and 95% B kept for 31 minutes; with the product eluting within 16.5-17.2 minutes post injection. Combined eluates were evaporated and dried under a high vacuum to give the purified product (17 mg, 74%). The HPLC analysis on ACE C18 column (5µ, 100 Å, 4.6×250 mm) confirmed satisfactory purity (≥95.0% at 254 nm) of the product 2: $t_R$=29.2 minutes, eluent: solvent A $H_2O$, solvent B MeCN; run with a linear gradient of B from 10% to 95% over 45 minutes, then 95% B for 20 minutes, elution rate 0.8 mL/minute. $^1$H NMR (DMSO-$d_6$) δ: 3.76 (s, 3H, $OCH_3$), 7.34-7.37 (m, 1H, aryl-H5'), 7.50-7.52 (m, 1H, aryl-H7), 7.54-7.56 (m, 1H, aryl-H6), 7.68-7.71 (m, 1H, aryl-H6'), 7.77-7.87 (m, 1H, aryl-H4), 7.97-8.01 (m, 2H, aryl-H2', aryl-H4'), 11.34-12.50 (m, 2H, —NH—, —NHCO—) ppm. $^{13}$C NMR (DMSO-d6) δ: 52.63 ($OCH_3$), 94.83 (aryl-C3'), 114.74 (aryl-C7), 116.29 (aryl-C4), 123.94 (aryl-C6), 128.79 (aryl-C6'), 130.11 (aryl-05'), 131.17 (aryl-05), 137.49 (aryl-C2'), 139.08 (aryl-C9), 140.20 (aryl-C8), 141.05, 141.19 (aryl-C4', aryl-C1'), 149.58 (aryl-C2), 154.49 (—NHCO—), 194.43 (CO) ppm. HR-MS (ESI), (m/e): calculated for $C_{16}H_{12}IN_3O_3$, 420.9923; [M+H]+ was found at 422.0054 within 13.1 ppm to its theoretical value.

Methyl N [5-(3'-trimethylstannylbenzoyl)-1H-benzimidazol-2-yl]carbamate (3)

A stirred solution of a crude iodide 2 (191 mg, 0.453 mmol, ~74% of 2 by HPLC analysis) in 25 mL of MeCN containing hexamethylditin (160 µL, 0.771 mmol), triethylamine (320 µL, 2.30 mmol) and dichlorobis(triphenylphosphine) palladium (II) catalyst (32 mg, 0.046 mmol), was gently refluxed under nitrogen until the starting 2 was no longer detectable by TLC (~3 hours). To remove the remaining catalyst, the reaction mixture after cooling to ambient temperature was passed through a thin layer of silica, repeatedly washed with MeCN (5×15 mL) and the solvent was evaporated. An excess of triethylamine was taken out by repeating the evaporation with toluene (3×25 mL) under vacuum at 60° C. To eliminate practically all of the unreacted hexamethylditin, the remaining solid was treated with EtOAc/hexanes solution (10 mL, 1:2, v/v) and the mixture was briefly sonicated, then centrifuged (2500 rpm, 15 minutes) and the solvent was carefully removed leaving a solid pellet. This process was repeated three times and after drying under a high vacuum, the remaining solid (153 mg) was analyzed by HPLC. The analyses indicated a multicomponent mixture containing one major new product (63%) along with ~12% of starting 2 and ~9% of 1. A final purification was completed after numerous injections of a crude product (30 mg, ~200 µg per injection) on an HPLC system equipped with a semipreparative Columbus C18 column (5µ, 100 Å, 10 mm×250 mm) eluted at 1.8 mL/minute flow rate with a linear gradient of MeCN in water from 45% to 60% in 19 minutes, then to 95% in 2 minutes and 95% MeCN kept for 20 minutes. The product 3 was collected within 18-19 minutes after the injection. Eluted fractions were evaporated and dried under a high vacuum to give the purified stannane 3 (16 mg, 53%). The HPLC analysis on ACE C18 column (5 µm, 100 Å, 4.6×250 mm) confirmed an adequate purity of the product 3 (≥95.0% at 254 nm): $t_R$=32.2 minutes, eluent: solvent A $H_2O$, solvent B $CH_3CN$; run with a linear gradient of B from 20% to 95% over 45 minutes, then 95% B for 20 minutes, elution rate 0.8 mL/minute. $^1$H NMR DMSO-$d_6$) δ: 0.32 (t, 3H, 3×$CH_3Sn$, $^2J_{H,Sn}$=29 Hz), 3.71 (s, 3H, $OCH_3$), 7.47-7.59 (m, 2H, aryl-H6, aryl-H5'), 7.61-7.66 (m, 1H, aryl-H4'), 7.69-7.74 (m, 1H, aryl-H6'), 7.77-7.86 (m, 1H, aryl-H4), 7.90-7.98 (m, 2H, aryl-H2', aryl-H7), 11.12-12.02 (m, 2H, —NH—, —NHCO—) ppm. $^{13}$C NMR (DMSO-$d_6$) δ: −4.27 (3×$CH_3Sn$), 52.81 ($OCH_3$), 117.32 (aryl-C7), 119.66 (aryl-C4), 125.14 (aryl-C6), 128.37 (aryl-05'), 130.14, 130.94 (aryl-C6', aryl-05), 136.28 (aryl-C2'), 138.72 (aryl-C3'), 139.18 (aryl-C9), 140.47 (aryl-C8), 141.15, 141.29 (aryl-C4', aryl-C1'), 148.88 (aryl-C2), 153.82 (—NHCO—), 194.45 (CO) ppm. HR-MS (ESI), (m/e): calculated for $C_{19}H_{21}N_3O_3Sn$, 459.0605; [M+H]+ was found at 459.0747 within 11 ppm to its theoretical value.

Methyl N-[5-(3'-[$^{125/131}$I]iodobenzoyl)-1H-benzimidazol-2-yl]carbamate (4)

Direct Radioiodination of 1

To a conical reaction vessel (0.5 mL volume) equipped with a magnetic stirring bar and a tight septum lid coated with Teflon®, a solution of N-chlorosuccinimide (NCS, 60 µg, 0.45 µmol) in MeCN (50 µL) was added and the solvent evaporated with a gentle stream of dried nitrogen. Subsequently a solution of 1 (166 µg, 0.56 µmol) in trifluoromethanesulfonic acid (250 µL, 2.85 µmol), was added under nitrogen and the reaction vial was tightly closed. A solution of Na$^{125}$I in 1×10$^{-5}$ M NaOH or Na$^{131}$I in 0.1 M NaOH (5 µL-20 µL, up to ~15 MBq to ~45 MBq) was introduced through a septum using a 20-µL syringe. The reaction temperature was slowly increased to 75° C. in 30 minutes. Periodically during this time, aliquots of the reaction mixture (5 µL-7 µL, ~185 kBq) were taken and transferred to a tube containing MeCN (50 μL) then quenched with a solution of $Na_2S_2O_5$ (50 mM, 20 μL) in 2 M NaOH and the progress of iodination was checked on HPLC (Bioscan/UV 254 nm detectors) using ACE C18 column (5 μm, 100 Å, 4.6×250 mm) eluted at 0.8 mL/minute with a linear gradient of MeCN in water from 10% to 95% MeCN over 45 minutes and 95% MeCN held for further 15 minutes; both solvents contained 0.07% TFA (v/v). The reaction was completed within 60 minutes at 75° C. The reaction mixture was cooled to room temperature, quenched with 50 mM $Na_2S_2O_5$ in 2 N NaOH (200 μL) and after neutralization to pH~4 was injected onto the HPLC system. The elution profile developed for monitoring the reaction progress was applied. The product 4 was collected within 27.5-29 minutes. The unreacted 1 eluting earlier (13.5-17 minutes) was cleanly separated from the product. Radioiodinations with $Na^{125}I$ were carried out within the 14.8 MBq-40.7 MBq range. Reactions with $Na^{131}I$ using 38.9 MBq-43.2 MBq $^{131}I$ produced $^{131}I$-4 with an average yield, after separation, reaching 62%.

Destannylation Method

Into a glass tube containing the stannane precursor 3 (100 μg, ~0.22 μmol) in MeCN (50 μL), a solution of $Na^{125}I$ in $1×10^{-5}$ M NaOH or $Na^{131}I$ in 0.1 M NaOH (5 μL-15 μL, 18.5 MBq-77.7 MBq) was added followed by $H_2O_2$ (5 μL, 30% water solution) and two minutes later, a solution of 0.1 N TFA in MeCN (50 μL). The resulting mixture, briefly vortexed and sonicated, was left in a closed tube for ~15 minutes at room temperature, then quenched with a water solution of $Na_2S_2O_5$ (50 mM, 20 μL), taken up into an HPLC syringe and the reaction tube washed twice with a mixture of $MeCN/H_2O$ (25 μL, 1:1, v/v). The reaction mixture combined with washes was injected onto the HPLC system. The separation of the products proceeded on Columbus C8 column (5 μm, 110 Å, 4.6×250 mm) equipped with Bioscan and UV detector at 220/254 nm and eluted at 0.8 mL/minute with a linear gradient of MeCN in water from 20% to 95% MeCN over 45 minutes and 95% MeCN held for 15 minutes longer. The radioiodide 4 was collected within 25-27 minutes after the injection. The excess of unreacted stannane 3 eluting between 31.5-34.5 minutes was fully separated from 4. Fractions containing the radioactive product were evaporated with a stream of nitrogen. Subsequent HPLC analyses of the product confirmed its high radiochemical purity (≥98%, Bioscan/UV 254 nm). Co-injections of purified 4 (~0.21 MBq) with nonradioactive analog 2 (~3.8 μg) have shown identical mobility of both compounds: $t_R$=28.8 minutes on ACE C8 100 Å (5 μm, 4.6×250 mm) eluted at 0.8 mL/minute with a linear gradient of MeCN from 10% to 95% MeCN over 45 minutes and kept at 95% MeCN for 15 minutes. To completely eliminate MeCN, fractions containing 4 were evaporated with a stream of nitrogen and 80 μL ethanol was added to the residue followed by 100 μL 10 mM potassium phosphate buffer, pH 6.1 (PB). The resulted mixture was vortexed and injected again on HPLC equipped with Luna C N reverse phase column (5μ, 4.6×250 mm) eluted at the rate of 0.8 mL/minute with a linear gradient of ethanol (EtOH) in 10 mM PB, pH 6.1, from 30% to 70% in 30 minutes and next from 70% to 95% of EtOH over 15 minutes. The product was collected within 22-25 minutes after the injection. In radioiodestannylations carried out with $Na^{125}I$ within the 18.5 MBq-77.7 MBq range, total of 140.6 MBq of $^{125}I$-4 was obtained. An average yield of the isolated product was 84%. Three radioiododestannylations performed with $Na^{131}I$ (29.6 MBq-48.1 MBq range) furnished 117 MBq of $^{131}I$-4 with yields exceeding 85%.

Stability of $^{125}I$-4 and $^{131}I$-4 in Human Serum

Sample Incubation 4 (370 KBq-740 kBq) in 20 μL 25% EtOH/PB (10 mM PB, pH 6.1) was added to the solution of human serum (1980 μL). The mixture was briefly vortexed and kept up to 19 hours at ambient temperature or in the cell culture incubator (37° C., 5% $CO_2$). At selected times, a 0.5-mL aliquot of the incubated mixture was withdrawn and analyzed by HPLC.

Preparation of Incubated Samples for HPLC Analyses

An aliquot of the incubation mixture (0.5 mL) was treated with MeCN (0.5 mL) to precipitate proteins, vortexed and centrifuged (2,000 rpm, 15 minutes). Aliquots of the supernatant (500 μL) were acidified to pH~6 with 0.05 M TFA (2-8 μL). The excess of MeCN was evaporated with a stream of nitrogen and 100 μL water added. This mixture was passed through a 0.2-μm filter and samples (~100 μL, 62.5 kBq-130 kBq) were injected on HPLC system.

HPLC Analyses of Supernatants

The HPLC analyses proceeded on Luna C N (5μ, 4.6×250 mm) column. Eluent: solvent A potassium phosphate buffer (10 mM, pH 6.1), solvent B EtOH; all samples were eluted at 0.8 mL/minute, initially with a gradient of EtOH from 30% to 70% for 30 minutes, then from 70% to 95% over the next 15 minutes with detection of radioactivity and UV at 280 nm.

Results

Two allied methods for the no-carrier-added radioiodination of 1 have been tested and effectively utilized: the direct electrophilic $^{125}I$- and $^{131}I$-iodination as well as radioiododestannylation of its organotin derivative 3 (FIG. 1).

The nonradioactive iodinated derivative 2 was prepared in a direct iodination of 1 with NIS in the excess of trifluoromethanesulfonic acid (triflic acid). This method involves the in situ formation of iodine(I) triflyl hypoiodite (Olah, et al., J. Org. Chem. (1993) 58(11):3194-3195). The protosolvated activated form of this potent superelectrophile was found to be effective in iodination of many deactivated aromatics (Olah, et al., J. Org. Chem. (1993) 58(11):3194-3195; Dalziel, et al., Inorg. Chem. (1973) 12(11):2707-2711; Kobayashi, et al., J. Chem. Res. Synop. (1977) 8:215). In addition, since NIS can be formed in situ from N-chlorosuccinimide and sodium iodide (Dewanjee, M. K., *Radioiodination: Theory, Practice, and Biomedical Applications.* Series: Developments in Nuclear Medicine 21. New York: Springer US; 1992, 110 pages; Coenen, et al., Radiochimica Acta (1983) 34:47-68), the radioiodination can be accomplished through the same reaction pathway generating protosolvated triflyl $[^{125/131}I]$hypoiodite as the electrophilic radioiodinating reagent. This approach to no-carrier-added electrophilic radioiodinations of monosubstituted weakly activated and deactivated benzenes (Mennicke, et al., J. Labelled Comp. Radiopharm. (2000) 43(7):721-737).

At first, methyl N-[5-(3'-iodobenzoyl)-1H-benzimidazol-2-yl]carbamate 2, the non-radioactive analogue of the target compound, was synthesized. The reaction progress at room temperature was slow and the quantity of iodinated product did not exceed 62% with ~31% of unreacted 1 remaining. The excess of triflic acid and gradual increase of the reaction temperature to 75° C. was necessary to achieve satisfactory levels of the iodination (~74%). To simplify workup of the reaction mixture by avoiding higher than necessary (4-6-fold) excess of triflic acid, nitromethane was used as a co-solvent, with no decrease of the iodination yield. HPLC analyses of all iodination mixtures, even after extensive modifications of the reaction time, temperature, and/or the excess of triflic acid, always revealed only one major product methyl N-[5-(3'-iodobenzoyl)-1H-benzimidazol-2-yl]carbamate 2, as determined by the NMR spectra, in yields ranging from 62%-74%. The leftover 1 (7%-30%) along with five small additional unidentified side-products (each ≤6%) were also present. No other isomers or multi-iodinated products were predominant. The selective formation of the meta regioisomer confirms the electrophilic character of this iodination. After partial crystallization from MeCN, the product was separated and further purified on the HPLC system. Attempted recrystallizations and flash column chromatography using normal phase silica gel failed due to low solubility of 2 in commonly used solvents.

Figures 2A, 2B, 2C:
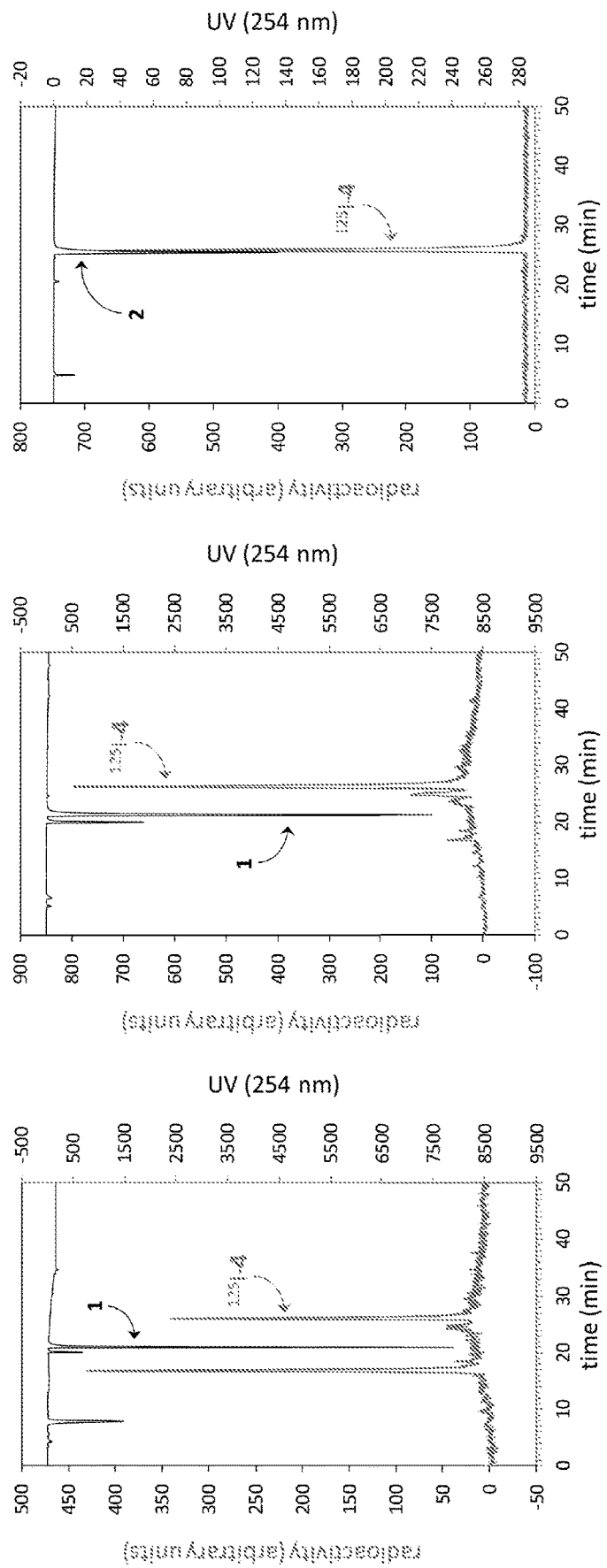
FIGS. 2A-2C provide HPLC analyses of $^{125}I$-4 synthesized using the direct radioiodination method.

The direct $^{125}$I- and $^{131}$I-iodination of 1 were accomplished in the same reaction pathway by generating protosolvated triflyl [$^{125/131}$I]hypoiodite from NCS/Na$^{125/131}$I in triflic acid. In the course of the initial trials, several reaction parameters were checked and adjusted to optimize the radioiodination yield. Periodically, aliquots from the reaction mixtures were taken and after quenching with a solution of Na$_2$S$_2$O$_3$/NaOH were injected on the HPLC system equipped with radioactivity and UV detectors to test the progress of radioiodination (FIGS. 2A and 2B). The reaction progress at room temperature was marginal (≤12% of 2 was detected after 180 minutes at 22° C.), nevertheless, it was critically important to start the radiolabeling at ambient temperature and then to increase the temperature gradually to 75° C. over a period of 30-45 minutes. The immediate heating of the mixture or shortened warming sequences triggered nearly 70% decrease of the yield. Extending the reaction time at 75° C. also led to the yield reduction with noticeable decomposition of the radioiodinated product. The highest radioiodination yields were achieved with amounts of NCS in the range of 0.4-0.6 µmol in 250 µL of triflic acid. For the best results, a conical reaction vessel was first coated inside with NCS through the evaporation of NCS solution in MeCN with a gentle stream of dried nitrogen, then a solution of 1 in triflic acid was added under nitrogen and the reaction vial was tightly closed. Solutions of Na$^{125}$I or Na$^{131}$I in NaOH were introduced through the septum with a syringe and the temperature of the stirred mixture was slowly increased to 75° C. The radiolabeling was completed in ~1 hour with an average yield of 4 reaching 62%. The correlation between the amount of 1 and the radiochemical yield was estimated using four concentrations of 1 ranging from 0.3 µmol to 0.8 µmol in 250 µL of triflic acid. The amount of ~0.5 µmol was found to be optimal. Higher concentrations did not increase the yield of the labeling and made the HPLC separation of the product more difficult. Several radioiodinations were carried out with Na$^{125}$I with the amount of $^{125}$I ranging from 14.8 MBq to 40.7 MBq to give a total of 159.4 MBq of $^{125}$I-4 with the average reaction yield>60%. Reactions conducted with Na$^{131}$I varied between 38.9 MBq-43.2 MBq $^{131}$I and produced a total of 163 MBq of $^{131}$I-4, also with the average isolated yield>60%. The reaction progress of the direct radioiodination with Na$^{125}$I conducted under the optimal conditions is shown in FIGS. 2A and 2B. To verify the identity of the isolated radioactive product, purified $^{125}$I-4 was co-injected with its nonradioactive analogue 2 and the eluates were monitored with the radioactivity and UV detectors (FIG. 2C). The identical retention time of 25.6 minutes was observed for 2 and $^{125}$I-4 confirming the identity of the radioactive product.

Figures 3A, 3B, 3C:
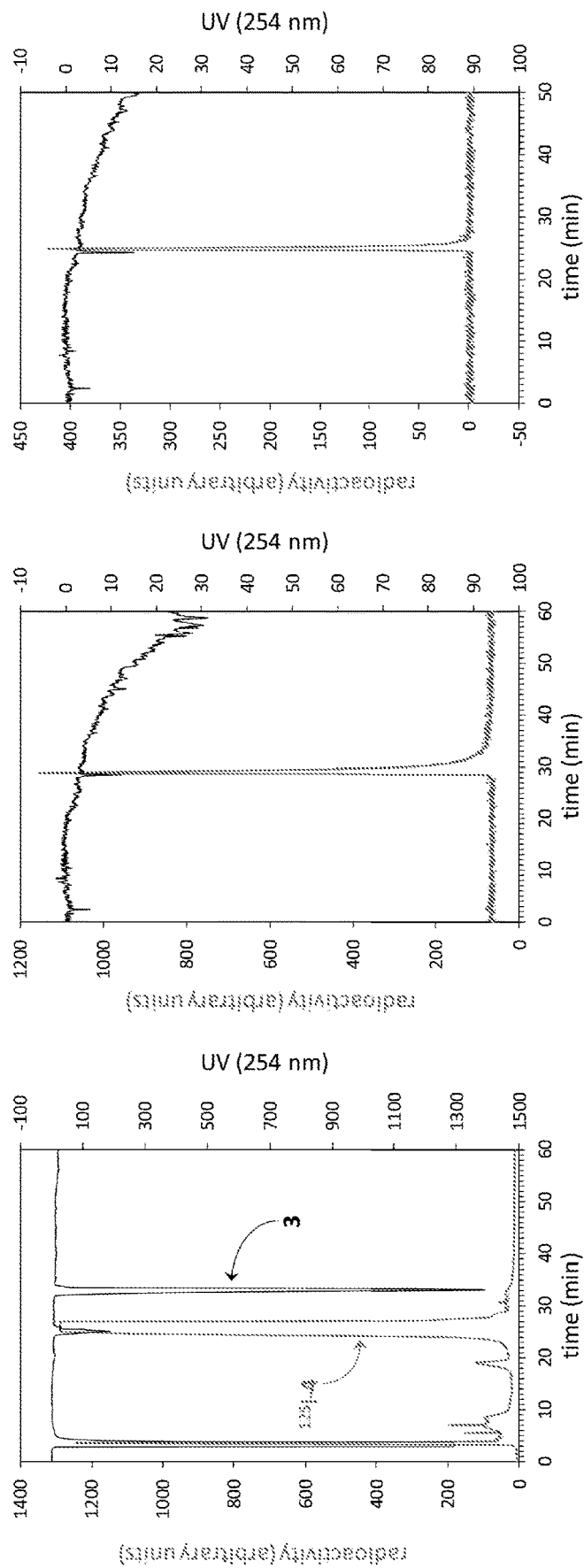
FIGS. 3A-3C provide HPLC analyses of $^{125}I$-4 synthesized using the radioiododestannylation method.

Starting from 2, the corresponding stannane-methyl N-[5-(3'-trimethylstannylbenzoyl)-1H-benzimidazol-2-yl]carbamate (3)—has been synthesized. This target compound was obtained through the typical stannylation of the iodide by hexamethylditin in the presence of triethylamine catalyzed by bis-(triphenylphosphine) palladium(II) dichloride (Baranowska-Kortylewicz, et al., J. Labelled Comp. Radiopharm. (1994) 34(6):513-521; Kortylewicz, et al., J. Med. Chem. (2009) 52(16):5124-5143; Kortylewicz, et al., Med. Chem. (2009) 5(2):171-181; Kortylewicz, et al., J. Med. Chem. (2012) 55(6):2649-2671). Stannylations were carried out under nitrogen in refluxed MeCN using crude iodide 2 containing ~7% of 1. The final purification of the stannane was accomplished on the HPLC system equipped with a semipreparative column after numerous injections of a crude product. Purified 3'-trimethylstannane 3 underwent the no-carrier-added radioiododestannylation with ease and high isolated yields of $^{125}$I-4 and $^{131}$I-4 were routinely achieved (~85%). Substantially increased hydrophobicity of stannane 3 compared to the iodinated compounds 2 and 4 allowed easy and complete separation of the excess of trimethyltin precursor 3 from the $^{125}$I- and $^{131}$I-iodinated products even when a large volume of the crude reaction mixture (up to 600 µL) was loaded onto the HPLC column for the final purification. The typical HPLC purification of $^{125}$I-4 from the destannylation mixture is shown in FIG. 3A. Analytical traces of $^{125}$I-4 in two solvent systems are shown in FIGS. 3B and 3C. The desired product $^{125}$I-4 was collected within 25-27 minutes after injection. The excess of unreacted tin precursor 3 eluted between 31.5-34.5 minutes and was fully separated from 4.

Radioiodinations with $^{125}$I and $^{131}$I were conducted with the radionuclide amounts ranging from 18.5 MBq to 77.7 MBq using 100 µg of the stannane 3 in each reaction. Reactions were conducted in a solution of 0.1% TFA in MeCN and hydrogen peroxide was used to oxidize sodium [$^{125/131}$I]iodide. A small amount of 1 (~1%) formed from the stannane 3 as the proton destannylated byproduct was detected in crude reaction mixtures. This amount of 1 increased to ~4% when the stannane sample was stored frozen for prolonged times (>3 months).

Figure 4C:
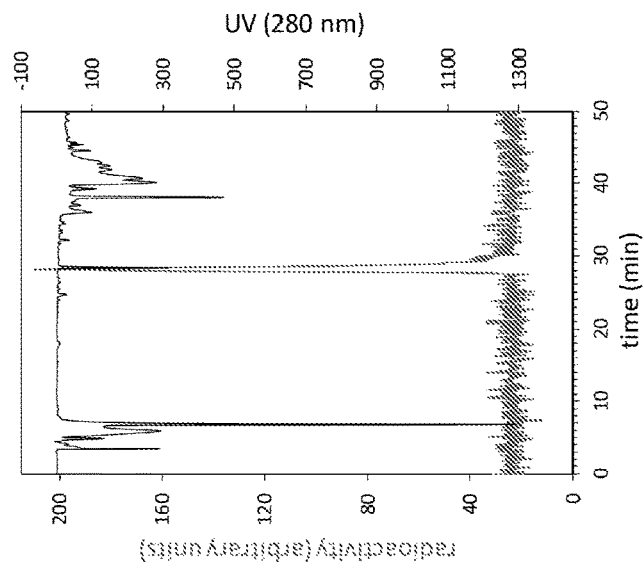
FIGS. 4A-4C show the stability of 4 incubated with human serum and cell culture medium and analyzed using HPLC.
Figure 4B:
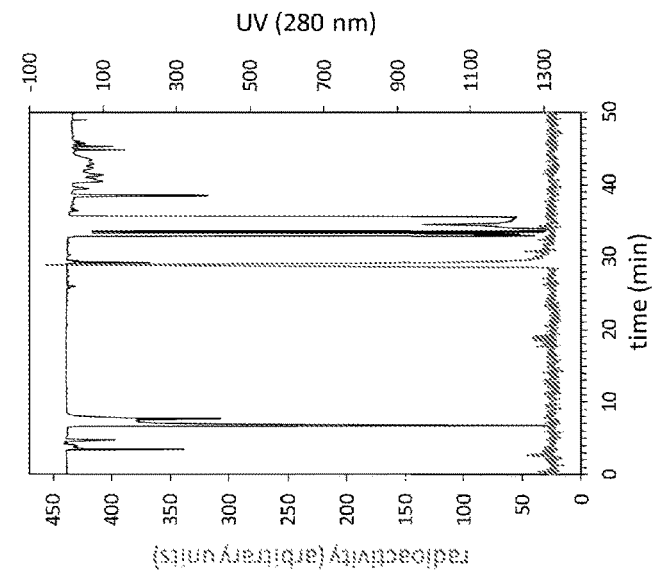
Figure 4A:
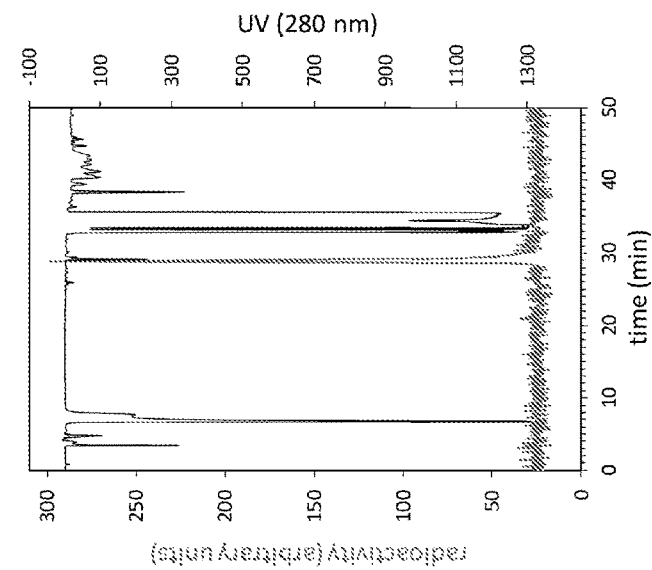

To assure compatibility with biological milieu such as required in the determination of stability of new drugs in human serum and cell culture experiments, radioactive products were purified on the HPLC system using USP-grade ethanol and phosphate buffer (FIG. 3C). In this solvent system on a Luna column, $^{125}$I-4 eluted at $t_R$=28.8 minutes with ≥98% radiochemical purity. The final radioactive 4 was passed through a 2-µm sterile filter before use. Stability studies performed in preparation to the in vivo evaluation of 4 indicate that $^{125}$I-4 and $^{131}$I-4 are stable in human serum. FIGS. 4A and 4B show examples of HPLC analyses of $^{125}$I-4 incubated in human serum for 5 hours and 17 hours. At both times, the radioactive trace indicates exclusively non-degraded $^{125}$I-4. Similar results were obtained in stability studies in cell culture media performed in preparation to in vitro evaluation of 4 (FIG. 4C).

The synthesis, purification and quality assurance methods of novel microtubule-targeted theranostic methyl N-[5-(3'-radiohalobenzoyl)-1H-benzimidazol-2-yl] carbamates were developed. The direct radioiodination method is more convenient for the synthesis of 4 radiolabeled with long-lived radiohalides. The process is lengthier but it does not require any precursors. The radioiododestannylation method is rapid and compatible with short-lived radiohalides such as $^{111}$At, $^{123}$I, or radioisotopes of Br. N-[5-(3'-radiohalobenzoyl)-1H-benzimidazol-2-yl]carbamates are stable in human serum and cell culture medium.

Example 2

Cytotoxicity and radiosensitizing properties of the non-radioactive analogue were determined. Specifically, the cytotoxicity of the nonradioactive analogue N-[5-(3'-iodobenzoyl)-1H-benzimidazol-2-yl]carbamate was measured. The nonradioactive drug was determined to be cytotoxic within a low nM range in human neuroblastoma cell lines and within a micromolar range in human glioblastoma cells lines.

This nonradioactive derivative is also an excellent radiosensitizer. For example, the administration of 1 micromolar N-[5-(3'-iodobenzoyl)-1H-benzimidazol-2-yl]carbamate to BE(2)-C neuroblastoma cells kills 89.8% of cancer cells after a 24 hour exposure. BE(2)-C neuroblastoma cells are a chemoresistant and radioresistant cell line derived from a highly aggressive and heavily pretreated neuroblastoma specimen from a small boy. When N-[5-(3'-iodobenzoyl)-1H-benzimidazol-2-yl]carbamate is combined with 4 Gy ionizing radiation (XRT) only 4.8% of cancer cells survive. Moreover, reproductive integrity assays showed that 30.63% cells survive 4 Gy XRT alone, 7.8% cells survive N-[5-(3'-iodobenzoyl)-1H-benzimidazol-2-yl]carbamate alone, but <0.9% survive the combined treatment of 4 Gy XRT and N-[5-(3'-iodobenzoyl)-1H-benzimidazol-2-yl]carbamate. Thus, the use of N-[5-(3'-iodobenzoyl)-1H-benzimidazol-2-yl]carbamate shows a more than additive effect (i.e., a synergistic effect).

The radiotoxicity of $^{131}$I-radiolabeled drug was also tested and it was determined that the radiotoxicity of $^{131}$I-radiolabeled drug is concentration- and time-dependent. At concentrations as low as 0.35 MBq/mL, very few colonies are produced after a 72 hour exposure in a colony-forming assay. The surviving fractions are as follows for SK-N-SH cells (a neuroblastoma cell line): 0.68±0.069 at 24 hours and 0.08±0.04 after 48 hours. There were no colonies in assays evaluated after a 72 hour exposure in this cell line. In a similar experiment using BE(2)-C cells, surviving fractions were as follows: 0.51±0.067 after a 24 hour exposure to 0.35 MBq, 0.06±0.02 after a 48 hour exposure to 0.35 MBq, and 0.010±0.004 after a 72 hour exposure to 0.29 MBq. At higher concentrations, there were no survivors. These results demonstrate the effectiveness of the radiohalide compound.

Example 3

Materials and Methods
Cell Survival and $LD_{50}$ Determination for Compounds 1 and 2

Compounds 1 or 2 dissolved in DMSO were added to the appropriate cell culture medium in concentrations ranging from 0 µM to 1.5 µM. Higher concentrations were not evaluated as the amount of DMSO required to maintain the drugs' solubility was not compatible with good cell culture conditions. The final concentration of DMSO was maintained at ≤0.5% in all flasks including controls. With each treatment group, duplicate flasks of control cells were grown and harvested alongside treated cells. Each treatment was tested in duplicate in at least two independent experiments (n=4-6 per concentration). Cell numbers were determined after 1 hour, 24 hours, and 48 hours of exposure to drugs using the trypan blue exclusion assay. Aliquots of cell suspension were mixed with a 0.2% solution of trypan blue in PBS (1/1; v/v) and counted in Cellometer® (Nexcelom Bioscience, Lawrence, Mass.). Lethal toxicity doses ($LD_{50}$) were estimated using the sigmoidal dose-response curve with variable slope and constant bottom and top values set at surviving fractions (SF) of 0 and 1, respectively (GraphPad Prism v. 7.04, La Jolla, Calif.). The reproductive integrity was also evaluated using a clonogenic survival assay.

Figure 5:
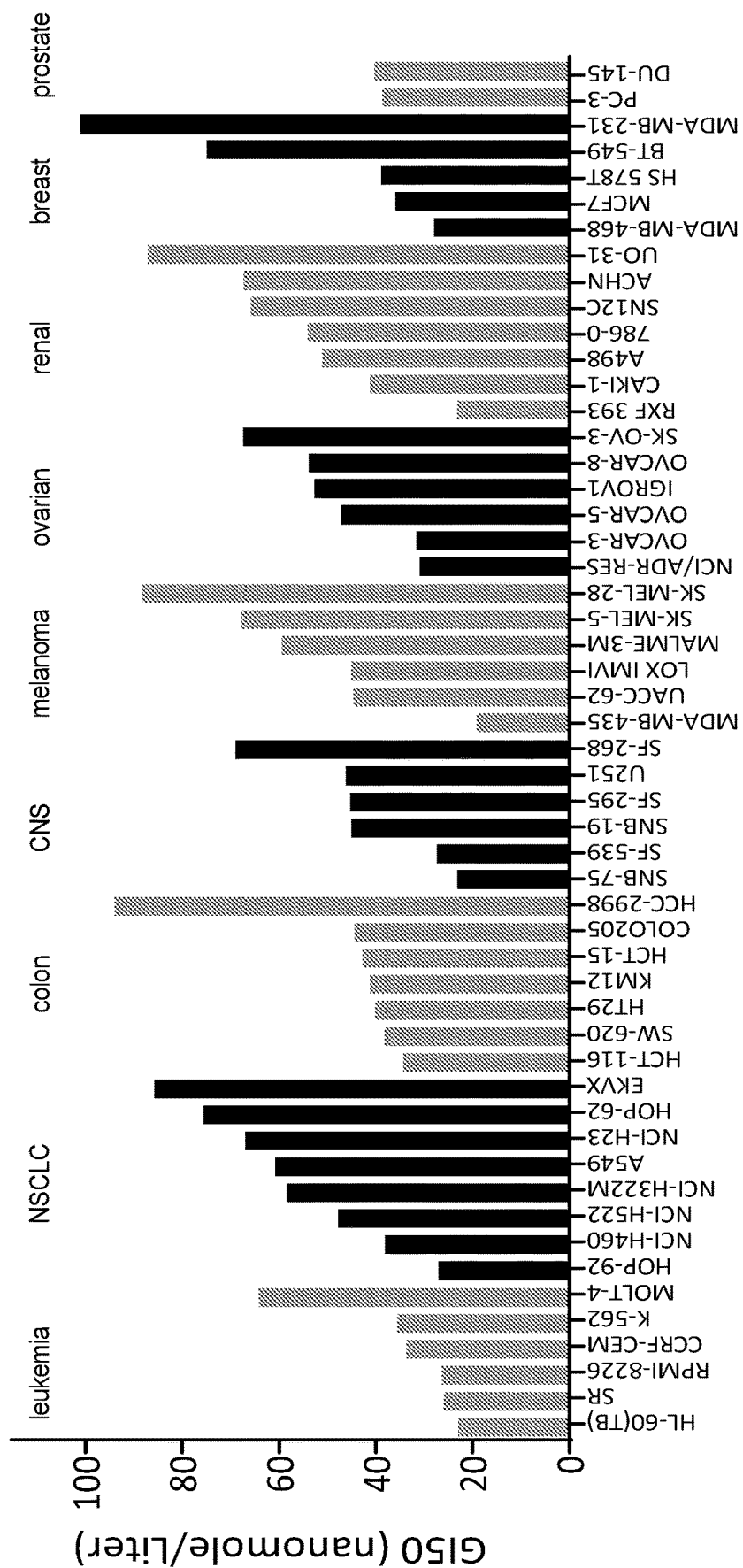
FIG. 5 provides the concentrations (nanomole/liter) required to inhibit by 50% growth of cancer cells (GI50) as measured with the National Cancer Institute (NCI) 60 cell five-dose screen assay.

Compound 1 was also evaluated by the NCI Developmental Therapeutics program using a 60 cell one-dose screen and NCI 60 cell five-dose screen. The methodology and data analyses are described in detail at: dtp.cancer.gov/discovery_development/nci-60/methodology. FIG. 5 provides the results of the screen, demonstrating nanomolar levels to inhibit growth of the indicated cancer cells by 50%.

Concentration- and Time-Dependent Uptake and Subcellular Distribution

The cell uptake was tested as a function of the radioactive concentration and time of exposure. With each treatment group, triplicate flasks of controls cells in medium without the radioactive drug were grown and harvested alongside treated cells. Aliquots of the radioactive medium were reserved for gamma counting to assess the initial radioactive concentration. Each treatment was tested in triplicate in at least two independent experiments. Groups of treated cells were cultured in radioactive medium for 1 hour, 24 hours, 48 hours, and 72 hours and either harvested at these times or the radioactive medium was removed and replaced with the appropriate nonradioactive medium and then flasks were returned to the incubator for additional 24 hours. Radioactive medium was collected for radioactivity determination, monolayers were washed with ice-cold PBS. Cells used in the subcellular distribution experiments were harvested by scarping and cell numbers were determined. The subcellular distribution of radioactivity was determined as described before using NE-PER™ nuclear and cytoplasmic extraction reagents (Pierce Biotechnology, Rockford, Ill.).

XRT Treatment

Compound 1 or 3 dissolved in DMSO was added to the appropriate cell culture medium at a final concentration of 1 µM. Alongside all treatment groups, which included: drug alone (n=4), 4 Gy XRT alone (n=4), and drug+XRT (n=4), quadruplicate flasks of controls cells in medium containing DMSO were grown and harvested under identical culture conditions. Each treatment was tested in at least two independent experiments. The final concentration of DMSO was maintained at 0.5% in all flasks including controls. Cells grown in monolayers (50%-60% confluent) were irradiated at the dose of 4 Gy delivered at the dose rate of 1.36 Gy/minute in a Mark I 68A irradiator (J. L. Shepherd & Associates, San Fernando, Calif.). At designated times after treatment, cells were harvested, their numbers determined and plated at 200 and 500 live cells in duplicate or quadruplicate T25 flasks per each treatment. Cells were left undisturbed for ~7 days after which time fresh medium was added and colonies were allowed to grow for up to 3 weeks. Colonies were washed with PBS, fixed with methanol, and stained with crystal violet. Briefly, colonies were washed with 5 mL ice-cold PBS, followed by 5 mL PBS/methanol (1:1; v/v), and fixed in 5 mL methanol for 10 minutes. Methanol was removed and flasks were left open to dry for a few hours. Crystal violet (3 mL; 0.25% in 1:1 PBS/methanol) was added to each flask to stain cells. After approximately 10 minutes, the dye was removed, flasks were rinsed with tap water followed by distilled water and were left to dry. Colonies were counted by two independent observers using the ImageJ software.

Effects of the treatment sequence on the cellular response was measured as follows: cells were plated in T25 flasks in three treatment groups A, B, and C (n=4 per group). Untreated control cells were also plated in T25 flasks (n=4 per group). On day 0, all cells were given media with 0.5% DMSO; cells in groups A and C were treated with 1 µM compound 3; cells in groups A and B were irradiated at 2 Gy. On day 1, cells in group A and its matching controls were harvested; cells were counted, their viability determined and SF calculated; cells in group B were given fresh medium with 1 µM compound 3 and their controls received fresh media with 0.05% DMSO; cells in group C and their controls received fresh media containing 0.5% DMSO; cells in group C were irradiated at 2 Gy. On day 2, cells in groups B and C alongside their controls were harvested. Cells were counted, their viability determined and SF calculated.

Cell Cycle Analyses

Control and treated cells were harvested, washed with PBS, 2×10$^6$ aliquots were transferred into test tubes, and centrifuged for 10 minutes at 1,000 rpm. Pellets were resuspended in 70% ethanol and kept at 4° C. overnight. Just before analyses, cells were centrifuged to remove ethanol, cell pellets were washed with PBS and centrifuged again. Telford reagent was added to cell pellets, gently vortexed and cells were incubated at 4° C. for 1 hour. Cell cycle analyses were done on the FACSCalibur™ flow cytometer (Becton Dickinson Immunocytometry Systems, San Jose, Calif.) at the UNMC Flow Cytometry Research Facility.

Animal Studies

U-87MG cells were injected subcutaneously (SQ) in the dorsal area of the female and male 8-weeks old athymic Ncr nu/nu mice (n=10 per group). When tumor volume reached ~150 mm$^3$ mice were randomized into treatment group and "sham" injected control group. The average tumor volumes on day 0 were 177±55 mm$^3$ and 141±25 mm$^3$ in the treatment group and untreated controls, respectively. Therapy mice received $^{131}$I-4 at an average dose of 14.5±2.3 MBq/mouse. Tumor volumes and body weights were measured three times per week. When one tumor in control mice exceeded the volume of 3000 mm$^3$ (i.e., 10% of the body weight), the experiment was terminated. Necropsy was performed. Tumor weights and tumor-associated radioactivity were determined. Blood was collected and hemoglobin and hematocrit values were measured. Tumors sections were also analyzed by macroautoradiography.

Results Cell survival and LD$_{50}$ determination for compounds 1 and 2 on four human cancer cell lines—BE(2)-C (neuroblastoma), SK-N-SH cells (neuroblastoma), U-87 MG (glioblastoma), and U137 MG. The results are provided in Table 1.

TABLE 1

LD50 values for compounds 1 and 2 in four human cancer cells lines

| cell line | 1 uM (std err) | 2 uM (std err) |
|---|---|---|
| BE(2)-C | 0.97 (0.15) | 0.02 (0.01) |
| SK-N-SH | 0.98 (0.76) | 1.29 (0.24) |
| U-87 MG | nd | 0.20 (0.06) |
| U137 MG | nd | 2.62 (1.35) |

The cell uptake of $^{131}$I-4 was tested as a function of the radioactive concentration and time of exposure. Groups of treated cells—BE(2)-C (neuroblastoma), SK-N-SH cells (neuroblastoma), and U-87 MG (glioblastoma)—were cultured in radioactive medium for 1 hour, 24 hours, 48 hours, and 72 hours. The results at the 48 hour timepoint are provided in Table 2.

TABLE 2

Extracellular and intracellular D$_{10}$ values in human cancer cells lines exposed to $^{131}$I-4 for 48 hours.

| | D$_{10}$ | | |
|---|---|---|---|
| cell line | extracellular MBq/mL | intracellular cpm/cell (std err) | intracellular decays/cell |
| BE(2)-C | 0.176 | 0.36 (0.05) | 3,010 (395) |
| SK-N-SH | 0.410 | 0.82 (0.09) | 7,620 (530) |
| U-87MG | 0.740 | 1.73 (0.34) | 14,760 (2,550) |

Figure 6A:
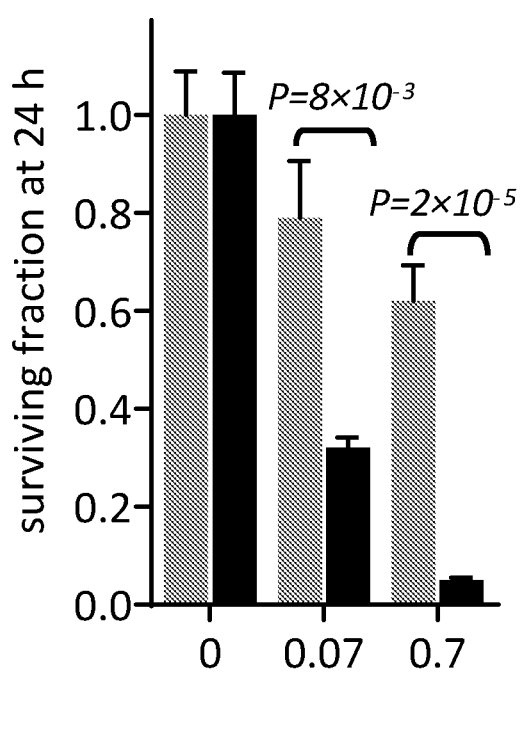
FIG. 6A provides a graph of the surviving fraction of SK-N-SH and BE(2)-C cells treated for 24 hours with 2.
Figure 6B:
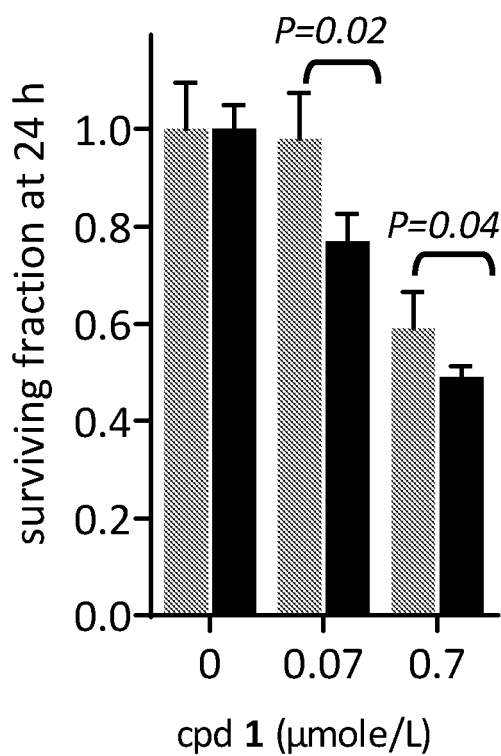
FIG. 6B provides a graph of the surviving fraction of SK-N-SH and BE(2)-C cells treated for 24 hours with compound 1.
Figure 6C:
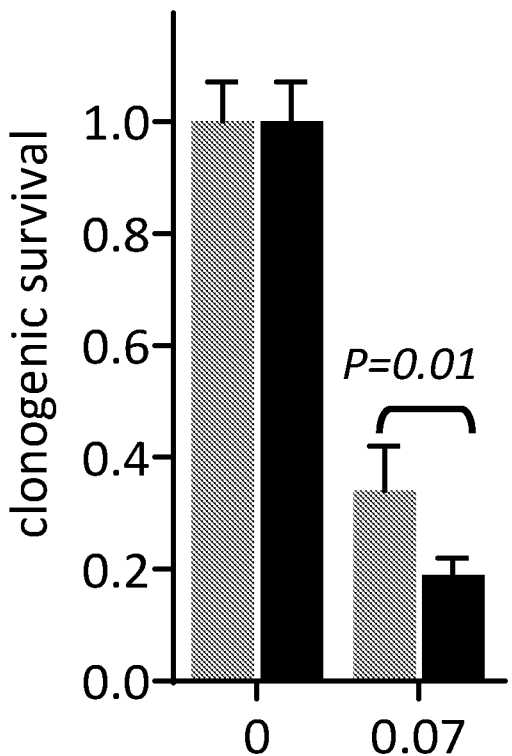
FIG. 6C provides a graph of the clonogenic survival of SK-N-SH and BE(2)-C cells treated with 1 µM 2.

The effects of compounds 1 and 2 on the cell cycle, survival, and morphology of SK-N-SH and BE(2)-C human neuroblastoma cells was also tested. FIG. 6A shows the concentration dependent survival of SK-N-SH and BE(2)-C cells treated for 24 hours with 2. FIG. 6B shows the concentration dependent survival of SK-N-SH and BE(2)-C cells treated for 24 hours with compound 1. FIG. 6C further shows the clonogenic survival of SK-N-SH and BE(2)-C cells treated with 1 µM 2. These results demonstrate the toxicity of 2 to cancer cells.

Figure 6D:
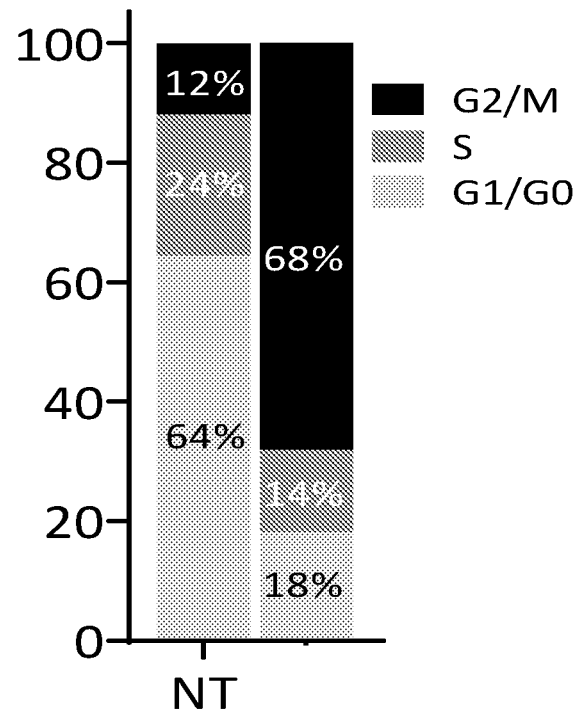
FIG. 6D provides a graph of the distribution of the cell cycle phases in BE(2)-C cells either not treated (NT) or treated with 2.
Figures 6E, 6F:
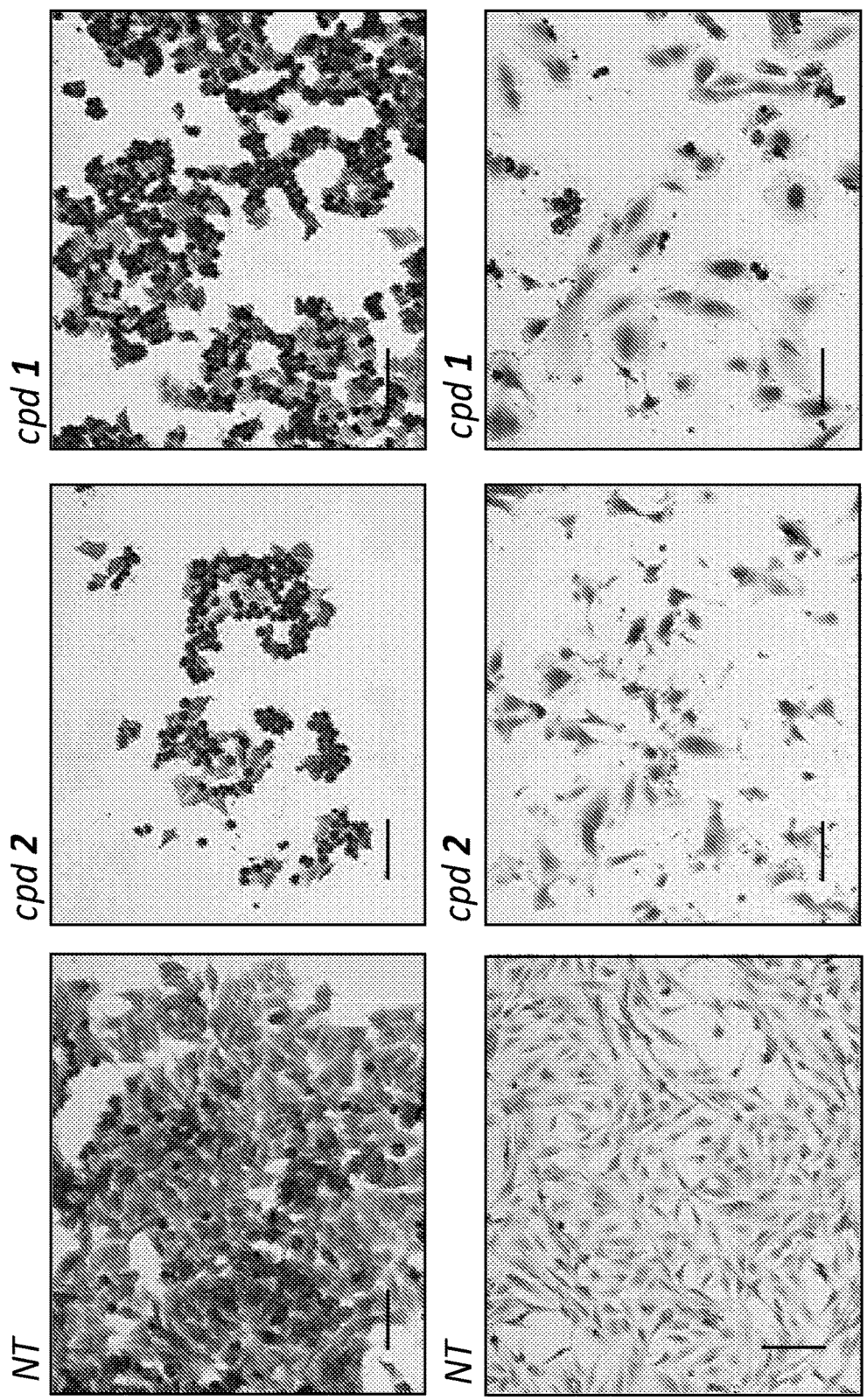
FIG. 6E provides images of BE(2)-C cells that were untreated (NT) or treated for 24 hours with 1 or 2 at 1 µM. 500 µm bar is shown in the left-hand corner.
FIG. 6F provides images of SK-N-SH cells that were untreated (NT) or treated for 24 hours with 1 or 2 at 1 µM. 500 µm bar is shown in the left-hand corner.

Cell cycle analyses of BE(2)-C cells were also performed. FIG. 6D provides the distribution of the cell cycle phases in BE(2)-C cells derived from the flow cytometry data of cells not treated or treated with 2. FIG. 6E provides the morphology of BE(2)-C cells that were untreated or treated for 24 hours with 1 or 2 at 1 µM. FIG. 6F provides the morphology of SK-N-SH cells that were untreated or treated for 24 hours with 1 or 2 at 1 µM. These results again demonstrate the toxicity of 2 to cancer cells.

Figure 7A:
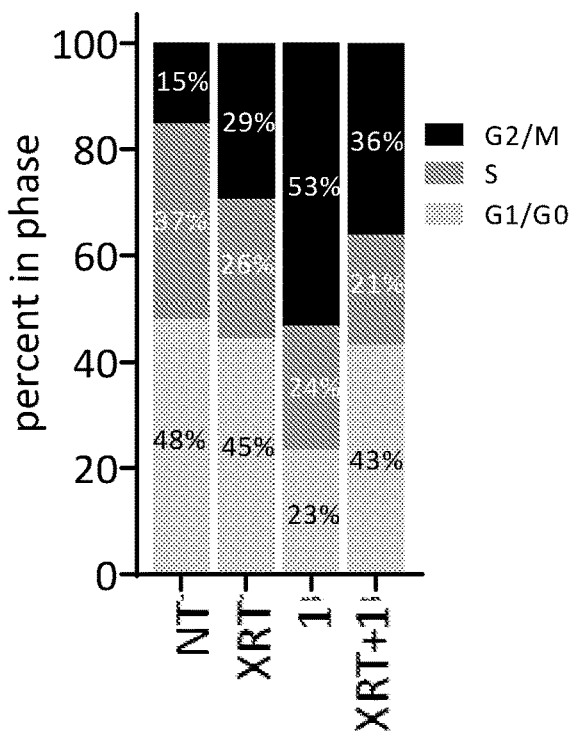
FIGS. 7A and 7B provide graphs of the distribution of the cell cycle phases in BE(2)-C and SK-N-SH cells, respectively, either not treated (NT), treated with a 4-Gy dose of ionizing radiation and harvested 24 hours later (XRT), treated for 24 hours with 1 at a concentration of 1 or treated with 1 at 1 µM for 24 hours, given fresh medium, irradiated at a dose of 4 Gy, and then harvested 24 hours later (XRT+1).
Figure 7B:
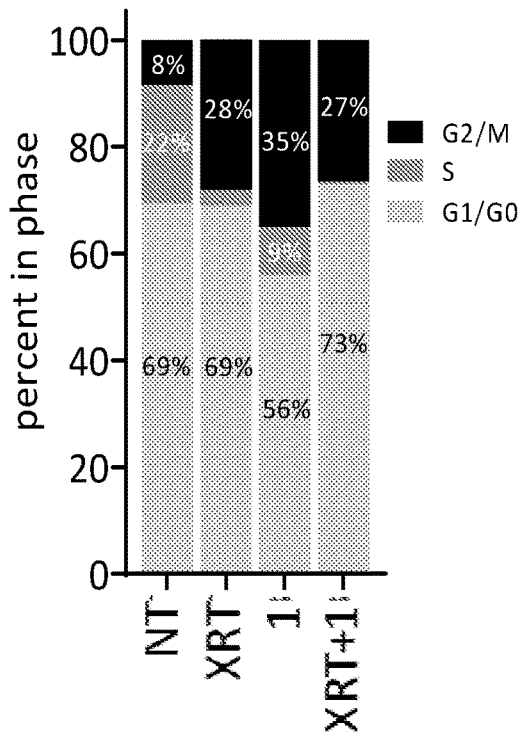
Figure 7C:
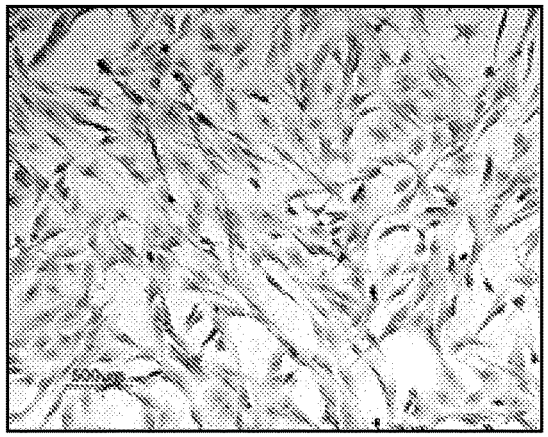
FIGS. 7C and 7D provide the morphology of untreated SK-N-SH cells (FIG. 7C) and SK-N-SH cells (FIG. 7D) treated with XRT and 1 µM. 500 µm bar is shown in the left-hand corner.
Figure 7D:
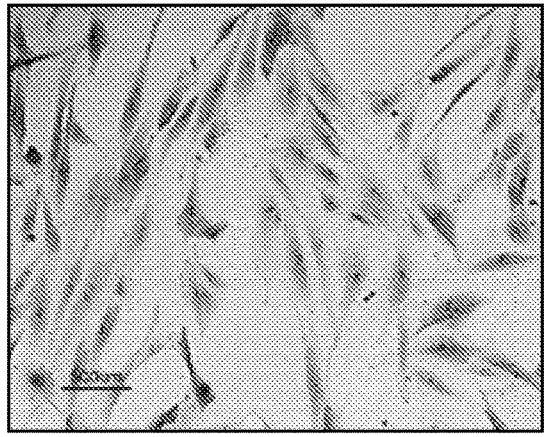
Figure 7E:
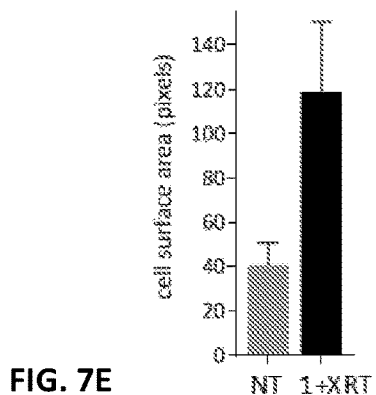
FIG. 7E provides a graph of cell surface area of SK-N-SH cells before (NT) and after treatment with 1 µM 1 and XRT.

The effects of compound 1, ionizing radiation and the combination thereof on the cell cycle and morphology of BE(2)-C and SK-N-SH human neuroblastoma cells was also determined. Cell cycle analyses were performed on BE(2)-C and SK-N-SH cells that were untreated, treated with a 4-Gy dose of ionizing radiation and harvested 24 hours later, treated for 24 hours with 1 at a concentration of 1 or treated with 1 at 1 µM for 24 hours, given fresh medium, irradiated at a dose of 4 Gy, and then harvested 24 hours later. FIGS. 7A and 7B provide the distribution of the cell cycle phases in BE(2)-C and SK-N-SH cells, respectively, derived from the flow cytometry data. FIGS. 7C and 7D provide the morphology of untreated SK-N-SH cell and SK-N-SH cells treated with XRT and 1 µM 1. The surface area of SK-N-SH cells before and after treatment with 1 µM 1 and XRT was measured using the ImageJ software (FIG. 7E).

Figure 8A:
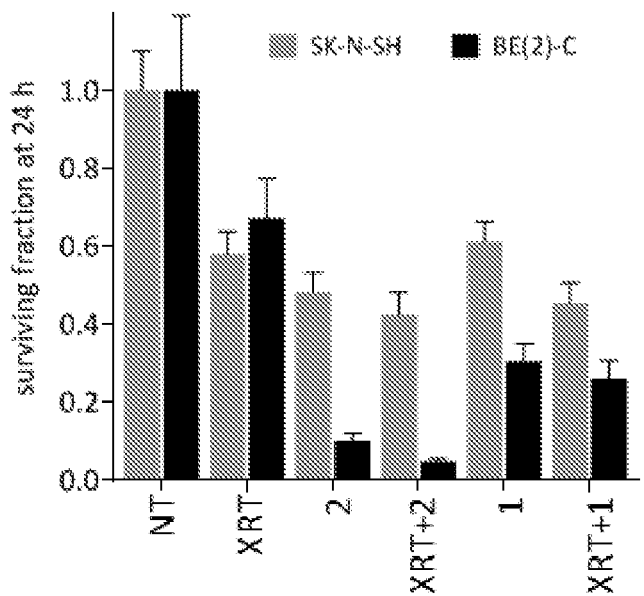
FIG. 8A provides a graph of surviving fraction of SK-N-SH cells (grey) and BE(2)-C cells (black) treated with either 1 µM 1 or 2 without and with ionizing radiation (XRT).
Figure 8B:
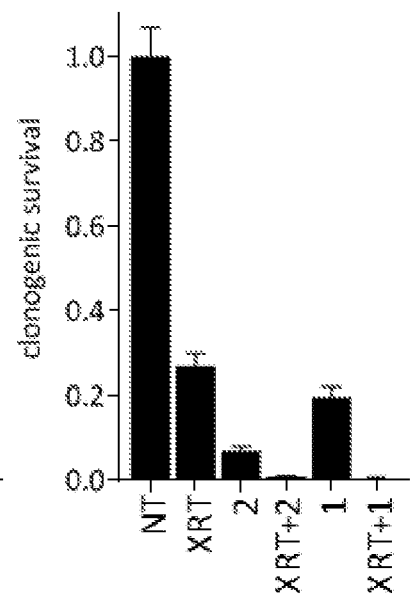
FIG. 8B provides a graph clonogenic survival of BE(2)-C cells treated with either 1 µM 1 or 2 without and with ionizing radiation (XRT).
Figure 8C:
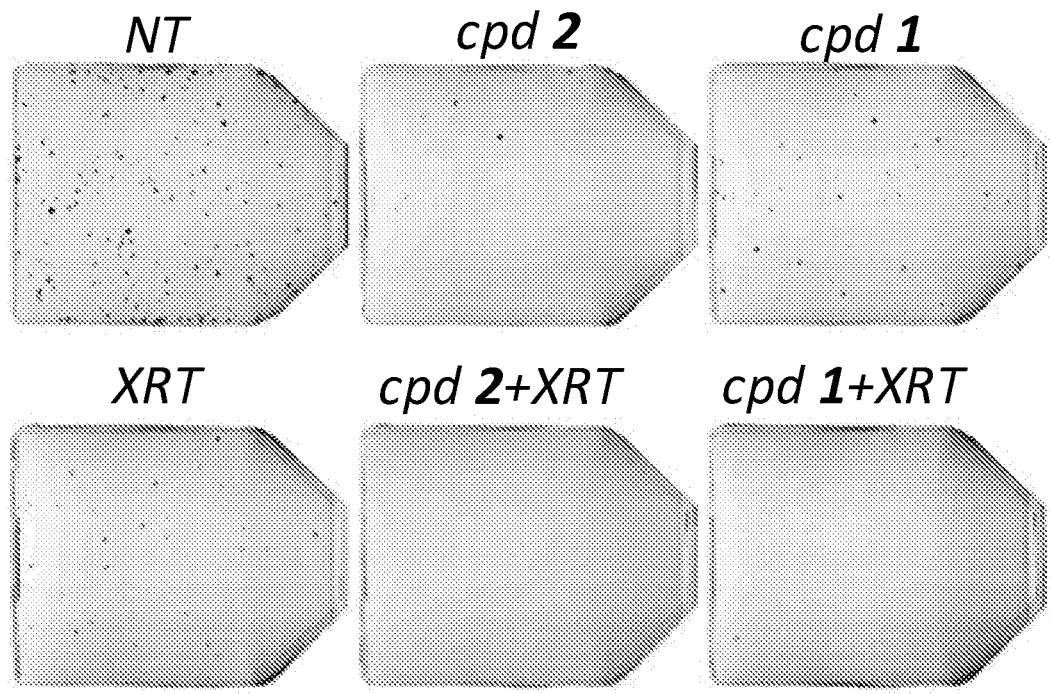
FIG. 8C provides images of the clonogenic survival assay.

The survival of neuroblastoma cells treated with either 1 µM 1 or 2 without and with ionizing radiation (XRT) was assayed. Surviving fractions of SK-N-SH and BE(2)-C cells 24 hours after the treatment were determined. As seen in FIG. 8A, 2 was very cytotoxic to the cancer cells, particularly in combination with irradiation. A clonogenic survival assay of BE(2)-C cells was also performed. BE(2)-C cells were either untreated, treated with a 4-Gy dose of ionizing radiation and harvested 24 hours later, treated for 24 hours with 1 µM 1 or 2, or treated with 1 µM 1 or 2 for 24 hours, given fresh medium, irradiated at a dose of 4 Gy, and harvested 24 hours later. As seen in FIGS. 8B and 8C, 2 was very cytotoxic to the cancer cells, particularly in combination with irradiation.

Figures 9A, 9B, 9C:
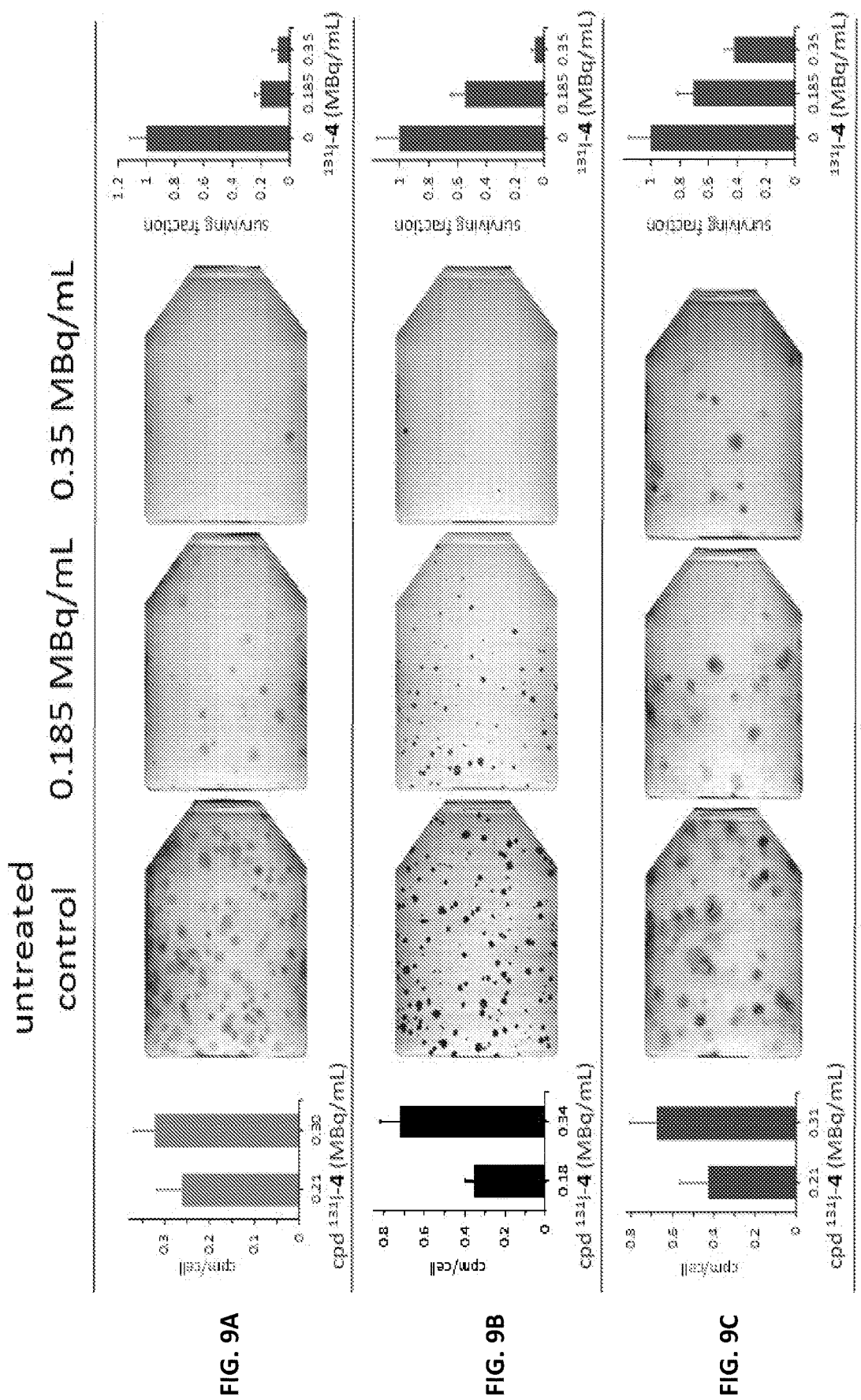
FIGS. 9A-9C provide images of SK-N-SH neuroblastoma (FIG. 9A), BE(2)-C neuroblastoma (FIG. 9B), and U-87 MG glioblastoma (FIG. 9C) untreated or treated with compound $^{131}$I-4 at 0.185 MBq/mL and 0.35 MBq/mL. Graphs of the cell uptake and clonogenic survival of the cells are also provided.

The survival of human neuroblastoma and glioblastoma cells either left untreated or treated with compound $^{131}$I-4 at 0.185 MBq/mL and 0.35 MBq/mL was determined. The cell uptake and clonogenic survival of SK-N-SH neuroblastoma, BE(2)-C neuroblastoma, and U-87 MG glioblastoma was also determined (FIGS. 9A-9C). As seen in FIGS. 9A-9C, $^{131}$I-4 is cytotoxic to neuroblastoma and glioblastoma cells.

U-87MG cells were injected subcutaneously (SQ) in the dorsal area of the female and male 8-weeks old athymic Ncr nu/nu mice (n=10 per group). Therapy mice received $^{131}$I-4 at an average dose of 14.5±2.3 MBq/mouse and tumor volumes and body weights were measured three times per week. The results are provided in Table 3. Mice treated with $^{131}$I-4 had dramatically decreases tumor growth compared to untreated control mice.

TABLE 3

Longitudinal changes of a U-87 MG xenograft volume in athymic Ncr nu/nu mice during treatment with $^{131}$I-4 and in control mice.

| | days after treatment | | | | |
|---|---|---|---|---|---|
| | 0 | 4 | 7 | 9 | 11 |
| $^{131}$I-4 | | | | | |
| avg (std err) (mm$^3$) | 177 (55) | 251 (88) | 277 (76) | 456 (165) | 444 (163) |
| median (mm$^3$) | 122 | 169 | 281 | 292 | 320 |
| CONTROLS | | | | | |
| avg (std err) (mm$^3$) | 141 (25) | 375 (99) | 940 (288) | 1080 (258) | 1409 (417) |
| median (mm$^3$) | 127 | 346 | 777 | 1173 | 1031 |

Figure 10A:
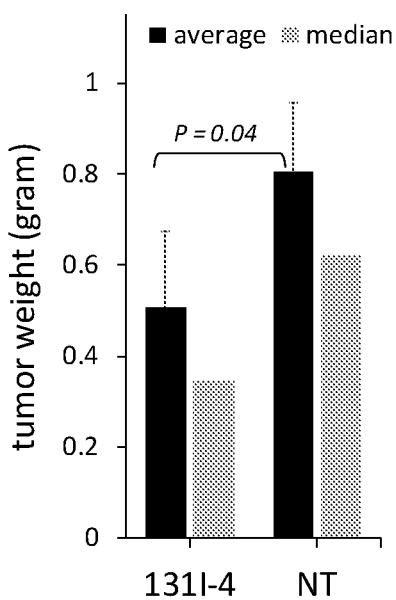
FIG. 10A provides a graph of the average and median weights of tumor extirpated from untreated control mice (NT) and $^{131}$I-4 treated mice at the terminal necropsy after the therapy.
Figure 10B:
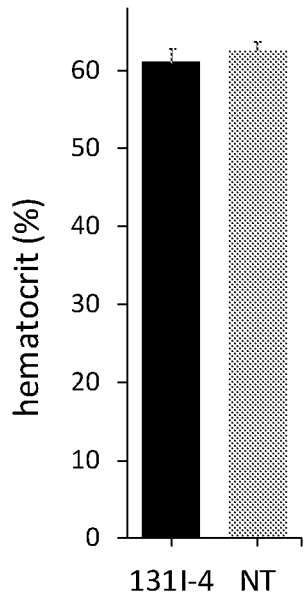
FIGS. 10B and 10C provide graphs of the hematocrit and hemoglobin values, respectively, in $^{131}$I-4-treated and control (NT) mice.
Figure 10C:
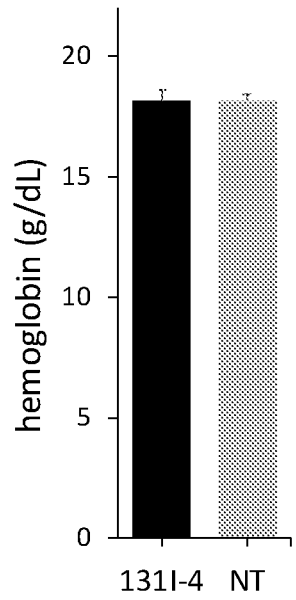
Figure 10D:
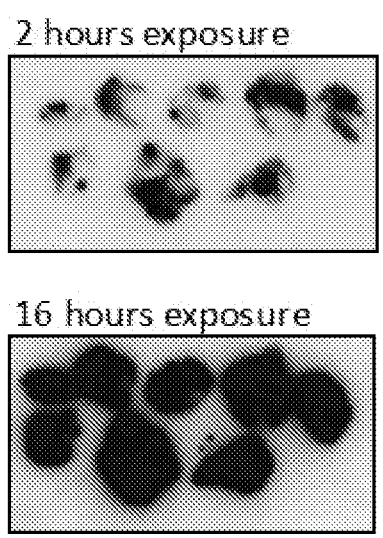
FIGS. 10D and 10E also show macroautoradiography of sections of two tumors extirpated at different exposure times.
Figure 10E:
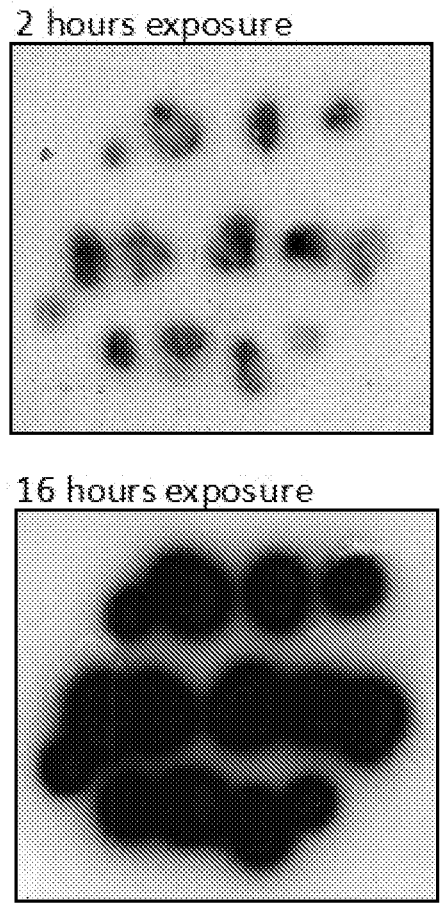

The average and median weights of tumor extirpated from untreated control mice (NT) and $^{131}$I-4 treated mice at the terminal necropsy after the therapy was also determined (FIG. 10A). Hematocrit and hemoglobin values in $^{131}$I-4-treated and control (NT) mice were also determined (FIGS. 10B and 10C). FIGS. 10D and 10E also show macroautoradiography of sections of two tumors extirpated. These results demonstrate that $^{131}$I-4 infiltrates tumors and that adverse reactions in the blood were not observed.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A compound of formula (I):

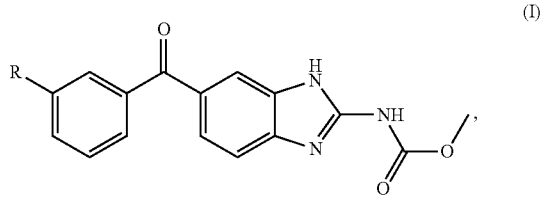

(I)

wherein R is iodine or an isotope of a halide.

2. The compound of claim 1, wherein said isotope is a stable isotope.

3. The compound of claim 1, wherein said isotope is a radioisotope.

4. The compound of claim 1, wherein said isotope is a radiohalide.

5. The compound of claim 4, wherein said radiohalide is selected from the group consisting of $^{18}$F, $^{74}$Br, $^{75}$Br, $^{76}$Br, $^{77}$Br, $^{81}$Br, $^{123}$I, $^{124}$I, $^{125}$I, $^{127}$I, $^{131}$I, and $^{211}$At.

6. A composition comprising a compound of claim 1 and a pharmaceutically acceptable carrier.

7. A method of treating, inhibiting, and/or a cancer in a subject in need thereof, said method comprising administering a compound of claim 1 to the subject.

8. The method of claim 7, wherein said compound is non-radioactive.

9. The method of claim 7, wherein said compound comprises a radioactive isotope.

10. The method of claim 7, said method further comprising administering radiation therapy to said subject.

11. The method of claim 8, said method further comprising administering radiation therapy to said subject.

12. A method for imaging and/or detecting a tumor in a subject, said method comprising:
   a) administering a compound of claim 1 to the subject, wherein said compound comprises a radioactive isotope; and
   b) detecting the presence of the radioactivity from said radioactive isotope from said subject,
   wherein the presence and/or location of the radioactivity provides for the detection and/or image of the tumor in said subject.

13. The method of claim 12, wherein the radioactive isotope is a gamma emitting isotope and step b) comprises performing a single photon emission computed tomography (SPECT) or scintigraphy.

14. The method of claim 12, wherein the radioactive isotope is a positron emitting isotope and step b) comprises performing a positron emitting tomography (PET).

15. A method for monitoring the progression of a cancer in a subject, said method comprising:
   a) administering a compound of claim 1 to the subject, wherein said compound comprises a radioactive isotope; and
   b) detecting the presence of the radioactivity from said radioactive isotope in said subject,
   wherein the presence and/or location of the radioactivity provides for the detection and/or image of the tumor in said subject; and
   wherein step b) or step a) and step b) are performed at different timepoints on the subject.

16. The compound of claim 1, wherein R is iodine.

17. The compound of claim 5, wherein said radiohalide is selected from the group consisting of $^{123}$I, $^{124}$I, $^{125}$I, $^{127}$I, and $^{131}$I.

* * * * *